United States Patent
Keefe et al.

(10) Patent No.: US 9,394,256 B2
(45) Date of Patent: Jul. 19, 2016

(54) BENZHYDROL-PYRAZOLE DERIVATIVES HAVING KINASE INHIBITORY ACTIVITY AND USES THEREOF

(71) Applicant: X-Chem, Inc., Waltham, MA (US)

(72) Inventors: Anthony D. Keefe, Cambridge, MA (US); Richard W. Wagner, Cambridge, MA (US); Matthew Clark, Bedford, MA (US); Ying Zhang, Lexington, MA (US); Diana Gikunju, Brockton, MA (US); John Cuozzo, Natick, MA (US); Heather Thomson, Arlington, MA (US)

(73) Assignee: X-Chem, Inc., Waltham, MA (US)

( * ) Notice: Subject to any disclaimer, the term of this patent is extended or adjusted under 35 U.S.C. 154(b) by 0 days.

(21) Appl. No.: 14/370,854

(22) PCT Filed: Jan. 9, 2013

(86) PCT No.: PCT/US2013/020834
§ 371 (c)(1),
(2) Date: Jul. 7, 2014

(87) PCT Pub. No.: WO2013/106432
PCT Pub. Date: Jul. 18, 2013

(65) Prior Publication Data
US 2015/0005345 A1 Jan. 1, 2015

Related U.S. Application Data

(60) Provisional application No. 61/584,569, filed on Jan. 9, 2012.

(51) Int. Cl.
*C07D 231/14* (2006.01)
*A61K 31/415* (2006.01)
*C07D 401/12* (2006.01)
*C07D 403/12* (2006.01)

(52) U.S. Cl.
CPC ............ *C07D 231/14* (2013.01); *A61K 31/415* (2013.01); *C07D 401/12* (2013.01); *C07D 403/12* (2013.01)

(58) Field of Classification Search
CPC .. C07D 231/14; C07D 401/12; C07D 403/12; A61K 31/415
See application file for complete search history.

(56) References Cited

U.S. PATENT DOCUMENTS

| | | | | |
|---|---|---|---|---|
| 6,319,940 B1 * | 11/2001 | Elbe et al. | | 514/406 |
| 6,534,532 B1 * | 3/2003 | Elbe et al. | | 514/370 |
| 6,716,881 B2 * | 4/2004 | Elbe et al. | | 514/617 |
| 2007/0219195 A1 | 9/2007 | Goldstein et al. | | |
| 2009/0105209 A1 | 4/2009 | Dewdney et al. | | |
| 2012/0270918 A1 | 10/2012 | Abecassis et al. | | |

FOREIGN PATENT DOCUMENTS

| WO | WO-2005/012256 A1 | 2/2005 |
|---|---|---|
| WO | WO-2011/001122 A2 | 1/2011 |

OTHER PUBLICATIONS

Barral, J Leukocyte Biology, vol. 94, Nov. 2013, p. 859-861.*
Shinohara, Cell, vol. 132, pp. 794-806, Mar. 2008.*
Vargas, Scandinavian J of Immunology, p. 130-139, vol. 78, 2013.*
International Preliminary Report on Patentability for International Application No. PCT/US2013/020834, dated Jul. 15, 2014 (6 pages).
International Search Report for International Application No. PCT/US2013/020834, dated Mar. 18, 2013 (2 pages).
Wyatt et al, "Identification of N-(4-piperidinyl)-4-(2,6-dichlorobenzoylamino)-1H-pyrazole-3-carboxamide (AT7519), a novel cyclin dependent kinase inhibitor using fragment-based X-ray crystallography and structure based drug design," J Med Chem. 51(16):4986-99 (2008).
Extended European Search Report for European Patent Application No. 13735755.4, mailed Jun. 15, 2015 (6 pages).

* cited by examiner

*Primary Examiner* — D M Seaman
(74) *Attorney, Agent, or Firm* — Clark & Elbing LLP

(57) ABSTRACT

The present invention features benzhydrol-pyrazole derivatives and related compounds having kinase inhibitory activity. The compounds of the invention, alone or in combination with other pharmaceutically active agents, can be used for treating or preventing various medical conditions, such as cancers, inflammatory disorders, or autoimmune disorders.

22 Claims, 8 Drawing Sheets

BENZHYDROL-PYRAZOLE DERIVATIVES HAVING KINASE INHIBITORY ACTIVITY AND USES THEREOF

CROSS-REFERENCE TO RELATED APPLICATIONS

This application is a national phase of International Application No. PCT/US2013/020834, filed Jan. 9, 2013, which claims benefit of U.S. Provisional Application No. 61/584,569, filed Jan. 9, 2012, which is hereby incorporated by reference in its entirety.

BACKGROUND OF THE INVENTION

The present invention relates to benzhydrol-pyrazole derivatives and related compounds having kinase inhibitory activity, as well as their therapeutic, diagnostic, and medical uses.

Bruton agammaglobulinemia tyrosine kinase (Btk or BTK) is a cytoplasmic kinase in the Tec family. Btk plays an important role in the development and regulation of lymphoid, myeloid, and mast cell lineages, such as by activating the B-cell receptor (BCR) signaling pathway, mediating cytokine receptor signaling, and participating in mast cell activation. However, activation or overactivation of Btk can contribute to or promote numerous diseases, including B-cell malignancies (e.g., Hodgkin's lymphoma, non-Hodgkin lymphoma, or chronic lymphocytic leukemia), inflammatory or autoimmune disorders (e.g., rheumatoid arthritis, systemic lupus erythematosus, or multiple sclerosis), and mast cell malignancies (e.g., pancreatic insulinoma). Thus, there is a need for new compounds that inhibit Btk and treatment methods using such compounds.

SUMMARY OF THE INVENTION

The invention features a compound having the formula:

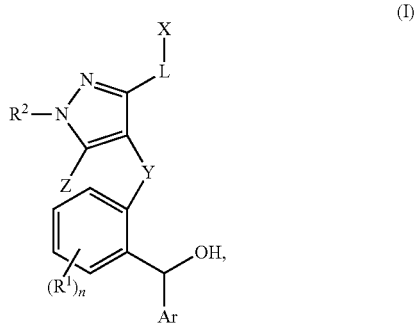

(I)

or a stereoisomer, pharmaceutically acceptable salt, or pharmaceutically acceptable prodrug thereof, where n is an integer from 0 to 4, and each $R^1$ is, independently, optionally substituted $C_{1-6}$ alkyl, optionally substituted $C_{2-6}$ alkenyl, optionally substituted $C_{2-6}$ alkynyl, optionally substituted halo-$C_{1-6}$ alkyl, optionally substituted $C_{1-6}$ alkoxy, optionally substituted $C_{2-6}$ alkenyloxy, optionally substituted $C_{2-6}$ alkynyloxy, optionally substituted halo-$C_{1-6}$ alkoxy, optionally substituted $C_{1-6}$ alkoxy-$C_{1-6}$ alkyl, optionally substituted $C_{1-7}$ acyl, optionally substituted $C_{1-7}$ acylamino, optionally substituted $C_{1-7}$ acyloxy, optionally substituted $C_{6-10}$ aryl, optionally substituted $C_{1-6}$ alk-$C_{6-10}$ aryl, optionally substituted amino, halo, cyano, nitro, hydroxy, or carboxyl;

Ar is optionally substituted $C_{6-10}$ aryl or optionally substituted $C_{1-12}$ heteroaryl;

$R^2$ is independently, H, optionally substituted $C_{2-6}$ alkenyl, optionally substituted $C_{2-6}$ alkynyl, optionally substituted halo-$C_{1-6}$ alkyl, optionally substituted $C_{1-6}$ alkoxy, optionally substituted $C_{2-6}$ alkenyloxy, optionally substituted $C_{2-6}$ alkynyloxy, optionally substituted halo-$C_{1-6}$ alkoxy, optionally substituted $C_{1-7}$ acyl, optionally substituted amino, halo, cyano, nitro, hydroxy, carboxyl, or an N-protecting group;

Y is selected from the group consisting of optionally substituted $C_{1-10}$ alkylene, optionally substituted $C_{1-10}$ heteroalkylene, —O—$CY^1Y^2$—, —$CY^1Y^2$—O—, —S—$CY^1Y^2$—, —$CY^1Y^2$—S—, —$NY^{N1}$—$CY^1Y^2$—, —$CY^1Y^2$—$NY^{N1}$—, —O—, —S—, —$NY^{N1}$—, —$NY^{N1}$—C(O)—, and —C(O)—$NY^{N1}$—, wherein each $Y^{N1}$ is, independently, H, optionally substituted $C_{1-6}$ alkyl, optionally substituted $C_{2-6}$ alkenyl, optionally substituted $C_{2-6}$ alkynyl, or an N-protecting group; and wherein each $Y^1$ and $Y^2$ is, independently, H, optionally substituted $C_{1-6}$ alkyl, optionally substituted $C_{2-6}$ alkenyl, or optionally substituted $C_{2-6}$ alkynyl; or wherein the combination of $Y^1$ and $Y^2$ can together form oxo or optionally substituted $C_{1-7}$ spirocyclyl (e.g., Y is —NH—$CY^1Y^2$—, where each $Y^1$ and $Y^2$ is, independently, H or optionally substituted $C_{1-6}$ alkyl or where the combination of $Y^1$ and $Y^2$ can together form oxo or optionally substituted $C_{1-7}$ spirocyclyl);

Z is H, optionally substituted $C_{1-6}$ alkyl, optionally substituted $C_{2-6}$ alkenyl, optionally substituted $C_{2-6}$ alkynyl, optionally substituted halo-$C_{1-6}$ alkyl, optionally substituted $C_{1-6}$ alkoxy, optionally substituted $C_{2-6}$ alkenyloxy, optionally substituted $C_{2-6}$ alkynyloxy, optionally substituted halo-$C_{1-6}$ alkoxy, optionally substituted $C_{1-6}$ alkoxy-$C_{1-6}$ alkyl, optionally substituted $C_{1-7}$ acyl, optionally substituted $C_{1-7}$ acylamino, optionally substituted $C_{1-7}$ acyloxy, optionally substituted $C_{6-10}$ aryl, optionally substituted $C_{1-6}$ alk-$C_{6-10}$ aryl, optionally substituted amino, halo, cyano, nitro, hydroxy, or carboxyl;

L is optionally substituted $C_{1-10}$ alkylene, optionally substituted $C_{1-10}$ heteroalkylene, —$NR^{L3}$—C(O)—, —C(O)—$NR^{L3}$—, —$NR^{L3}$—$CR^{L1}R^{L2}$—, —$CR^{L1}R^{L2}$—$NR^{L3}$—, or a bond, where each $R^{L1}$ and $R^{L2}$ is, independently, H, optionally substituted $C_{1-6}$ alkyl, optionally substituted $C_{2-6}$ alkenyl, optionally substituted $C_{2-6}$ alkynyl; or where the combination of $R^{L1}$ and $R^{L2}$ can together form oxo or optionally substituted $C_{1-7}$ spirocyclyl; and where each $R^{L3}$ is, independently, H, optionally substituted $C_{1-6}$ alkyl, optionally substituted $C_{2-6}$ alkenyl, optionally substituted $C_{2-6}$ alkynyl, or an N-protecting group (e.g., L is —NH—C(O)—, —C(O)—NH—, —NH—$CR^{L1}R^{L2}$—, —$CR^{L1}R^{L2}$—NH—, or a bond, where each $R^{L1}$ and $R^{L2}$ is, independently, H or optionally substituted $C_{1-6}$ alkyl or where the combination of $R^{L1}$ and $R^{L2}$ can together form oxo or optionally substituted $C_{1-7}$ spirocyclyl); and X is optionally substituted $C_{1-6}$ alkyl, optionally substituted $C_{3-8}$ cycloalkyl, optionally substituted $C_{6-10}$ aryl, or optionally substituted $C_{1-12}$ heterocyclyl.

In some embodiments, n is an integer from 0 to 2; Ar is optionally substituted $C_{6-10}$ aryl or optionally substituted $C_{1-12}$ heteroaryl; each $Y^1$ and $Y^2$ is, independently, H or optionally substituted $C_{1-6}$ alkyl; Z is H, optionally substituted $C_{1-6}$ alkyl, optionally substituted halo-$C_{1-6}$ alkyl, or halo; L is —NH—C(O)—, —C(O)—NH—, —NH—$CR^{L1}R^{L2}$—, —$CR^{L1}R^{L2}$—NH—, or a bond, where each $R^{L1}$ and $R^{L2}$ is, independently, H or optionally substituted $C_{1-6}$ alkyl; and X is optionally substituted $C_{1-6}$ alkyl, optionally substituted $C_{6-10}$ aryl, or optionally substituted $C_{1-12}$ heterocyclyl.

In some embodiments, the compound has a structure selected from:

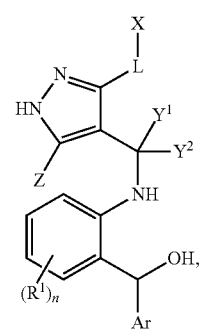

(Ia)

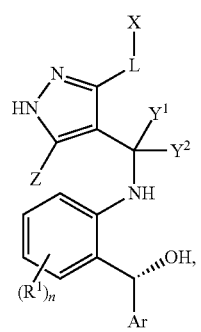

(Ib)

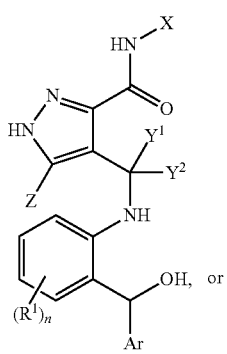

(IIa)

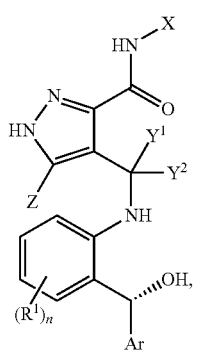

(IIb)

or a stereoisomer, pharmaceutically acceptable salt or pharmaceutically acceptable prodrug thereof. In particular embodiments, the compound has the structure of formula (Ib) or (IIb).

In some embodiments, the compound has a structure selected from:

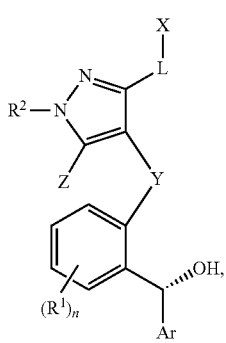

(I-2)

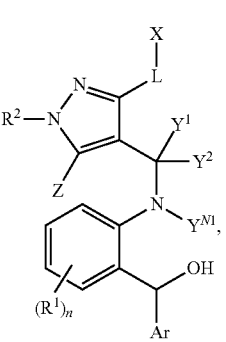

(Ia-2)

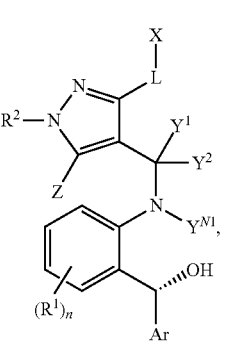

(Ib-2)

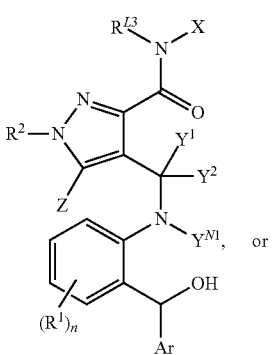

(IIa-2)

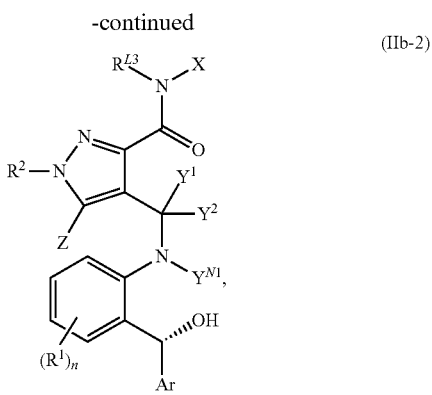

(IIb-2)

or a stereoisomer, pharmaceutically acceptable salt or pharmaceutically acceptable prodrug thereof, where $R^1$, $R^2$, n, Ar, L, $R^{L3}$, X, Y, $Y^1$, $Y^2$, $Y^{N1}$, Z, if present, are as described herein. In some embodiments, each $R^2$, $R^{L3}$, and $Y^{N1}$, is, independently, H, optionally substituted $C_{1-6}$ alkyl, optionally substituted $C_{2-6}$ alkenyl, optionally substituted $C_{2-6}$ alkenyl, or any described herein. In particular embodiments, the compound has the structure of formula (Ib-2) or (IIb-2).

In some embodiments, n is an integer from 0 to 2 (e.g., 0, 1, or 2). In some embodiments, each $R^1$ is, independently, optionally substituted $C_{1-6}$ alkyl, optionally substituted halo-$C_{1-6}$ alkyl, optionally substituted $C_{1-6}$ alkoxy, optionally substituted halo-$C_{1-6}$ alkoxy, optionally substituted $C_{1-7}$ acyl, optionally substituted $C_{1-7}$ acylamino, optionally substituted $C_{1-7}$ acyloxy, optionally substituted $C_{6-10}$ aryl, optionally substituted amino, halo, cyano, nitro, hydroxy, or carboxyl, e.g., optionally substituted $C_{1-6}$ alkyl, optionally substituted halo-$C_{1-6}$ alkyl, optionally substituted $C_{1-6}$ alkoxy, optionally substituted halo-$C_{1-6}$ alkoxy, optionally substituted amino, halo, cyano, nitro, hydroxy, or carboxyl.

In some embodiments, Ar has the formula:

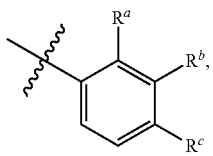

(III)

where the combination of $R^a$ and $R^b$ or the combination of $R^b$ and $R^c$ can together form optionally substituted $C_{6-10}$ aryl or optionally substituted $C_{1-12}$ heterocyclyl.

In other embodiments, Ar is optionally substituted $C_{1-12}$ heteroaryl (e.g., selected from the group of optionally substituted phenyl, optionally substituted pyridyl, optionally substituted pyrimidinyl, optionally substituted pyrazinyl, optionally substituted pyridazinyl, optionally substituted naphthyl, optionally substituted indenyl, optionally substituted anthryl, optionally substituted phenanthryl, optionally substituted quinolyl, optionally substituted isoquinolyl, optionally substituted quinoxalinyl, optionally substituted quinazolinyl, optionally substituted cinnolinyl, optionally substituted phthalazinyl, and optionally substituted quinolizinyl). In some embodiments, Ar is optionally substituted phenyl, optionally substituted naphthyl, optionally substituted quinolyl, or optionally substituted isoquinolyl (e.g., substituted with $C_{1-6}$ alkyl, halo-$C_{1-6}$ alkyl, $C_{1-6}$ alkoxy, halo-$C_{1-6}$ alkoxy, or halo). In other embodiments, Ar is unsubstituted $C_{1-12}$ heteroaryl (e.g., selected from the group of phenyl, pyridyl, pyrimidinyl, pyrazinyl, pyridazinyl, naphthyl, indenyl, anthryl, phenanthryl, quinolyl, isoquinolyl, quinoxalinyl, quinazolinyl, cinnolinyl, phthalazinyl, and quinolizinyl).

In some embodiments, each of $Y^1$, $Y^2$, and Z, if present, is, independently, H or optionally substituted $C_{1-6}$ alkyl, or where the combination of $Y^1$ and $Y^2$ can together form oxo or spirocyclopropyl. In particular embodiments, each of $Y^1$, $Y^2$, and Z is H, or both $Y^1$ and $Y^2$ are H. In some embodiments, Z is H.

In some embodiments, L is $-NH-C(O)-$, $-C(O)-NH-$, $-NH-CR^{L1}R^{L2}-$, $-CR^{L1}R^{L2}-NH-$, or a bond, where each $R^{L1}$ and $R^{L2}$ is, independently, H, optionally substituted $C_{1-6}$ alkyl, halo-$C_{1-6}$ alkyl, $C_{1-6}$ alkoxy, or halo-$C_{1-6}$ alkoxy, or where the combination of $R^{L1}$ and $R^{L2}$ can together form oxo or optionally substituted $C_{1-7}$ spirocyclyl.

In other embodiments, L is $-O-CR^{L1}R^{L2}-$, $-R^{L1}R^{L2}-O-$, $-S-CR^{L1}R^{L2}-$, $-CR^{L1}R^{L2}-S-$, $-NR^{L3}-CR^{L1}R^{L2}-$, $-CR^{L1}R^{L2}-NR^{L3}-$, $-O-$, $-S-$, $-NR^{L3}-$, $-NR^{L3}-C(O)-$, and $-C(O)-NR^{L3}-$, wherein each $R^{L3}$ is, independently, H, optionally substituted $C_{1-6}$ alkyl, optionally substituted $C_{2-6}$ alkenyl, optionally substituted $C_{2-6}$ alkynyl, or an N-protecting group, and wherein each $R^{L1}$ and $R^{L2}$ is, independently, H, optionally substituted $C_{1-6}$ alkyl, optionally substituted $C_{2-6}$ alkenyl, or optionally substituted $C_{2-6}$ alkynyl, or wherein the combination of $R^{L1}$ and $R^{L2}$ can together form oxo or optionally substituted $C_{1-7}$ spirocyclyl. In some embodiments, L is selected from the group consisting of optionally substituted $C_{1-6}$ alkylene, $-NH-C(O)-$, $-C(O)-NH-$, $-NH-CR^{L1}R^{L2}-$, and $-CR^{L1}R^{L2}NH-$, where each $R^{L1}$ and $R^{L2}$ is, independently, H or any described herein (e.g., H or optionally substituted $C_{1-6}$ alkyl); or where the combination of $R^{L1}$ and $R^{L2}$ can together form oxo or optionally substituted $C_{1-7}$ spirocyclyl.

In other embodiments, L is optionally substituted $C_{1-10}$ heteroalkylene (e.g., $-(CR^{L1}R^{L2})_{LA}-NR^{L3}-(CR^{L1}R^{L2})_{LB}-$, $-(CR^{L1}R^{L2})_{LA}-O-(CR^{L1}R^{L2})_{LB}-$, $-(CR^{L1}R^{L2})_{LA}-S-(CR^{L1}R^{L2})_{LB}-$, $-(CR^{L1}R^{L2})_{LA}-NR^{L3}-C(O)-(CR^{L1}R^{L2})_{LB}-$, or $-(CR^{L1}R^{L2})_{LA}-NR^{L3}-C(O)-NR^{L3}-(CR^{L1}R^{L2})_{LB}-$, where LA is an integer from 0 to 10, LB is an integer from 0 to 10, and the sum of LA and LB is an integer between 1 to 10 and where $R^{L1}$, $R^{L2}$, and $R^{L3}$ are as described herein). In particular embodiments, L is $-(CR^{L1}R^{L2})_{0-5}-NR^{L3}-(CR^{L1}R^{L2})_{1-5}-$, $-(CR^{L1}R^{L2})_{1-5}-NR^{L3}-(CR^{L1}R^{L2})_{0-5}-$, $-(CR^{L1}R^{L2})_{0-5}-O-(CR^{L1}R^{L2})_{1-5}-$, $-(CR^{L1}R^{L2})_{1-5}-O-(CR^{L1}R^{L2})_{0-5}-$, $-(CR^{L1}R^{L2})_{0-5}-S-(CR^{L1}R^{L2})_{1-5}-$, $-(CR^{L1}R^{L2})_{1-5}-S-(CR^{L1}R^{L2})_{0-5}-$, $-(CR^{L1}R^{L2})_{0-5}-NR^{L3}-C(O)-(CR^{L1}R^{L2})_{1-5}-$, $-(CR^{L1}R^{L2})_{1-5}-NR^{L3}-C(O)-(CR^{L1}R^{L2})_{0-5}-$, $-(CR^{L1}R^{L2})_{0-5}-NR^{L3}-C(O)-NR^{L3}-(CR^{L1}R^{L2})_{1-5}$, or $-(CR^{L1}R^{L2})_{1-5}-NR^{L3}-C(O)-NR^{L3}-(CR^{L1}R^{L2})_{0-5}$. In other embodiments, L is $-(CH_2)_{0-5}-NR^{L3}-(CH_2)_{1-5}-$, $-(CH_2)_{1-5}-NR^{L3}-(CH_2)_{0-5}-$, $-(CH_2)_{0-5}-O-(CH_2)_{1-5}-$, or $-(CH_2)_{1-5}-O-(CH_2)_{0-5}-$. In further embodiments, each $R^{L3}$ is, independently, H, optionally substituted $C_{1-6}$ alkyl, optionally substituted $C_{2-6}$ alkenyl, or optionally substituted $C_{2-6}$ alkynyl (e.g., unsubstituted $C_{1-6}$ alkyl).

In some embodiments, X is optionally substituted $C_{6-10}$ aryl (e.g., optionally substituted phenyl, e.g., unsubstituted phenyl or phenyl substituted with a substituent selected from the group consisting of $C_{1-6}$ alkyl, halo-$C_{1-6}$ alkyl, $C_{1-6}$ alkoxy, halo-$C_{1-6}$ alkoxy, halo, $C_{1-12}$ heterocyclyl, $(CH_2)_m-CO_2R^{X1}$, $-(CH_2)_m-C(O)-NR^{X1}R^{X2}$, and $-(CH_2)_m-NR^{X1}-C(O)-R^{X2}$, where m is an integer from 0 to 4 and each $R^{X1}$ and $R^{X2}$ is, independently, H or optionally substituted $C_{1-6}$ alkyl) or optionally substituted $C_{1-12}$ heteroaryl (e.g., selected from the group of optionally substituted quinoxalinyl, optionally substituted quinazolinyl, optionally substituted cinnolinyl, optionally substituted phthalazinyl, optionally substituted quinolyl, optionally substituted isoquinolyl, optionally substituted benzoxazolyl, optionally substituted benzimidazolyl, optionally substituted benzothiazolyl, optionally substituted benzothiadiazolyl, optionally substituted indolyl, optionally substituted indazolyl, optionally substituted benzofuranyl, optionally substituted isobenzofuranyl, and optionally substituted benzothienyl). In particular embodiments, X is unsubstituted $C_{6-10}$ aryl (e.g., phenyl, naphthyl, or any described herein) or unsubstituted $C_{1-12}$ heteroaryl (e.g., selected from the group of quinoxalinyl, quinazolinyl, cinnolinyl, phthalazinyl, quinolyl, isoquinolyl, benzoxazolyl, benzimidazolyl, benzothiazolyl, benzothiadiazolyl, indolyl, indazolyl, benzofuranyl, isobenzofuranyl, and benzothienyl).

In some embodiments, the compound has a formula provided in Table 1, or a stereoisomer, pharmaceutically acceptable salt, or pharmaceutically acceptable prodrug thereof.

In some embodiments, the compound of the invention has an $IC_{50}$ value less than about 1.0 µM (e.g., less than about 0.9 µM, less than about 0.75 µM, less than about 0.5 µM, less than about 0.3 µM, less than about 0.25 µM, less than about 0.2 µM, less than about 0.15 µM, less than about 0.1 µM, less than about 0.09 µM, less than about 0.08 µM, less than about 0.05 µM, less than about 0.04 µM, less than about 0.03 µM, less than about 0.025 µM, less than about 0.0015 µM, or less than about 0.001 µM). In some embodiments, the compound has an $IC_{50}$ value from about 0.02 to about 1.0 µM (e.g., from about 0.02 µM to about 0.9 µM, from about 0.02 µM to about 0.75 µM, from about 0.02 µM to about 0.5 µM, from about 0.02 µM to about 0.3 µM, from about 0.02 µM to about 0.25 µM, from about 0.02 µM to about 0.2 µM, from about 0.02 µM to about 0.15 µM, from about 0.02 µM to about 0.1 µM, from about 0.02 µM to about 0.09 µM, from about 0.02 µM to about 0.08 µM, from about 0.02 µM to about 0.05 µM, from about 0.02 µM to about 0.04 µM, from about 0.02 µM to about 0.03 µM, or from about 0.02 µM to about 0.025 µM). In some embodiments, the compound has an $IC_{50}$ value from about 0.0001 µM to about 0.9 µM (e.g., from about 0.0001 µM to about 0.8 µM, from about 0.0001 µM to about 0.5 µM, from about 0.0001 µM to about 0.3 µM, from about 0.0001 µM to about 0.2 µM, from about 0.0001 µM to about 0.1 µM, from about 0.0001 µM to about 0.09 µM, from about 0.0001 µM to about 0.08 µM, from about 0.0001 µM to about 0.05 µM, from about 0.0001 µM to about 0.04 µM, from about 0.0001 µM to about 0.03 µM, from about 0.0001 µM to about 0.025 µM, from about 0.0001 µM to about 0.015 µM, from about 0.0001 µM to about 0.01 µM, from about 0.0001 µM to about 0.005 µM, 0.0002 µM to about 0.9 µM, from about 0.0002 µM to about 0.8 µM, from about 0.0002 µM to about 0.5 µM, from about 0.0002 µM to about 0.3 µM, from about 0.0002 µM to about 0.2 µM, from about 0.0002 µM to about 0.1 µM, from about 0.0002 µM to about 0.09 µM, from about 0.0002 µM to about 0.08 µM, from about 0.0002 µM to about 0.05 µM, from about 0.0002 µM to about 0.04 µM, from about 0.0002 µM to about 0.03 µM, from about 0.0002 µM to about 0.025 µM, from about 0.0002 µM to about 0.015 µM, from about 0.0002 µM to about 0.01 µM, from about 0.0002 µM to about 0.005 µM, about 0.0005 µM to about 0.9 µM, from about 0.0005 µM to about 0.8 µM, from about 0.0005 µM to about 0.5 µM, from about 0.0005 µM to about 0.3 µM, from about 0.0005 µM to about 0.2 µM, from about 0.0005 µM to about 0.1 µM, from about 0.0005 µM to about 0.09 µM, from about 0.0005 µM to about 0.08 µM, from about 0.0005 µM to about 0.05 µM, from about 0.0005 µM to about 0.04 µM, from about 0.0005 µM to about 0.03 µM, from about 0.0005 µM to about 0.025 µM, from about 0.0005 µM to about 0.015 µM, from about 0.0005 µM to about 0.01 µM, from about 0.0005 µM to about 0.005 µM, from about 0.0005 µM to about 0.002 µM, from about 0.0005 µM to about 0.0015 µM, or from about 0.0005 µM to about 0.001 µM).

The invention also features a pharmaceutical composition comprising a compound of formula (I), (I-2), (Ia), (Ia-2), (Ib), (Ib-2), (IIa), (IIa-2), (IIb), or (IIb-2), or a stereoisomer, pharmaceutically acceptable salt, or pharmaceutically acceptable prodrug thereof, and a pharmaceutically acceptable excipient.

The invention further features a method of treating or prophylactically treating a condition in a subject (e.g., a human subject) in need thereof, where the method includes administering an effective amount of a compound of the invention, or a stereoisomer, pharmaceutically acceptable salt, or pharmaceutically acceptable prodrug thereof, or a pharmaceutical composition thereof to the subject. Examples of such conditions include a B-cell associated disease or a mast cell associated disease (e.g., a cancer, an inflammatory disorder, or an autoimmune disorder associated with B-cell or mast cell activation), cancer (e.g., any described herein), or an inflammatory or autoimmune disorder (e.g., any described herein).

Non-limiting exemplary cancers include leukemia, including acute myeloid leukemia (AML), acute lymphocytic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), and B-cell prolymphocytic leukemia (B-PLL); lymphomas, including Hodgkin and non-Hodgkin lymphoma, such as B-cell lymphomas (e.g., diffuse large B-cell lymphoma (e.g., mediastinal (thymic) large B-cell lymphoma and intravascular large B-cell lymphoma), follicular lymphoma, small lymphocytic lymphoma (SLL), chronic lymphocytic leukemia/small lymphocytic lymphoma (CLL/SLL), mantle cell lymphoma (e.g., relapsed or refractory), marginal zone B-cell lymphomas, Burkitt lymphoma, lymphoplasmacytic lymphoma, hairy cell leukemia, primary central nervous system (CNS) lymphoma, primary effusion lymphoma, and lymphomatoid granulomatosis); myelomas, including multiple myeloma, plasmacytoma, localized myeloma, and extramedullary myeloma; and other cancers, such as pancreatic neoplasms, including pancreatic exocrine tumors (e.g., ductal adenocarcinoma, signet ring cell carcinomas, hepatoid carcinomas, colloid carcinomas, undifferentiated carcinomas, and undifferentiated carcinomas with osteoclast-like giant cells), pancreatic cystic neoplasms (e.g., mucinous cystadenoma, serous cystadenoma, and mucinous ductal ectasia), pancreatic neuroendocrine tumors (e.g., insulinoma, glucagonoma, gastrinoma, VIPoma, and somatostatinoma), papillary cystic neoplasms of the pancreas, lymphoma of the pancreas, and acinar cell tumors of the pancreas, or any described herein.

Non-limiting exemplary inflammatory or autoimmune disorders include autoimmune arthritis (e.g., rheumatoid arthritis, psoriatic arthritis, ankylosing spondylitis, Still's disease, juvenile arthritis, and mixed and undifferentiated connective tissue diseases), autoimmune hemolytic and thrombocytopenic states (e.g., autoimmune-mediated hemolytic anemia, e.g., warm autoimmune hemolytic anemia, cold autoimmune hemolytic anemia, cold agglutinin disease, and paroxysmal cold hemoglobinuria), autoimmune hepatitis, Behçet's disease, chronic idiopathic thrombocytopenic purpura (ITP), glomerulonephritis, Goodpasture's syndrome (and associated glomerulonephritis and pulmonary hemorrhage), idiopathic thrombocytopenic purpura (ITP) (e.g., acute ITP or chronic ITP), inflammatory bowel disease (including Crohn's disease and ulcerative colitis), multiple sclerosis, psoriasis (including psoriatic lesions in the skin), systemic lupus erythematosus (and associated glomerulonephritis), and vasculitis (including antineutrophil cytoplasmic antibodies-associated vasculitis, immune complex mediated vasculitis, and Wegener's granulomatosis), or any described herein.

DEFINITIONS

The term "about," as used herein, means+/-10% of the recited value.

The term "acyl," as used herein, represents a hydrogen or an alkyl group (e.g., a haloalkyl group), as defined herein, that is attached to the parent molecular group through a carbonyl group, as defined herein, and is exemplified by formyl (i.e., a carboxyaldehyde group), acetyl, propionyl, butanoyl and the like. Exemplary unsubstituted acyl groups include from 1 to 7 carbons. In some embodiments, the alkyl group is further substituted with 1, 2, 3, or 4 substituents as described herein.

The term "acylamino," as used herein, represents an acyl group, as defined herein, attached to the parent molecular group though an amino group, as defined herein (i.e., $N(R^{N1})_2$—C(O)—R, where R is H or an optionally substituted $C_{1-6}$ alkyl group). Exemplary unsubstituted acylamino groups include from 1 to 7 carbons. In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl.

The term "acyloxy," as used herein, represents an acyl group, as defined herein, attached to the parent molecular group though an oxygen atom (i.e., —O—C(O)—R, where R is H or an optionally substituted $C_{1-6}$ alkyl group). Exemplary unsubstituted acyloxy groups include from 1 to 7 carbons. In some embodiments, the alkyl group is further substituted with 1, 2, 3, or 4 substituents as described herein, and/or the amino group is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, alkyl, or aryl.

The term "alkaryl," as used herein, represents an aryl group, as defined herein, attached to the parent molecular group through an alkylene group, as defined herein. Exemplary unsubstituted alkaryl groups are from 7 to 16 carbons (e.g., $C_{1-6}$ alk-$C_{6-10}$ aryl). In some embodiments, the alkylene and the aryl each can be further substituted with 1, 2, 3, or 4 substituent groups as defined herein for the respective groups. Other groups preceded by the prefix "alk-" are defined in the same manner, where "alk" refers to a $C_{1-6}$ alkylene, unless otherwise noted, and the attached chemical structure is as defined herein.

The term "alkcycloalkyl" represents a cycloalkyl group, as defined herein, attached to the parent molecular group through an alkylene group, as defined herein (e.g., an alkylene group of 1-4, 1-6, or 1-10 carbons). In some embodiments, the alkylene and the cycloalkyl each can be further substituted with 1, 2, 3, or 4 substituent groups as defined herein for the respective group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like. Alkenyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkenyloxy" represents a chemical substituent of formula —OR, where R is a $C_{2-6}$ alkenyl group, unless otherwise specified. In some embodiments, the alkenyl group can be further substituted with 1, 2, 3, or 4 substituent groups as defined herein.

The term "alkheteroaryl" refers to a heteroaryl group, as defined herein, attached to the parent molecular group through an alkylene group, as defined herein. In some embodiments, the alkylene and the heteroaryl each can be further substituted with 1, 2, 3, or 4 substituent groups as defined herein for the respective group. Alkheteroaryl groups are a subset of alkheterocyclyl groups.

The term "alkheterocyclyl" represents a heterocyclyl group, as defined herein, attached to the parent molecular group through an alkylene group, as defined herein. Exemplary unsubstituted alkheterocyclyl groups are from 2 to 18 (e.g., 2 to 17, 2 to 16, 3 to 15, 2 to 14, 2 to 13, or 2 to 12) carbons. In some embodiments, the alkylene and the heterocyclyl each can be further substituted with 1, 2, 3, or 4 substituent groups as defined herein for the respective group.

The term "alkoxy" represents a chemical substituent of formula —OR, where R is a $C_{1-6}$ alkyl group, unless otherwise specified. In some embodiments, the alkyl group can be further substituted with 1, 2, 3, or 4 substituent groups as defined herein.

The term "alkoxyalkyl" represents an alkyl group that is substituted with an alkoxy group. Exemplary unsubstituted alkoxyalkyl groups include between 2 to 12 carbons (e.g., $C_{1-6}$ alkoxy-$C_{1-6}$ alkyl). In some embodiments, the alkyl and the alkoxy each can be further substituted with 1, 2, 3, or 4 substituent groups as defined herein for the respective group.

The term "alkyl," as used herein, is inclusive of both straight chain and branched chain saturated groups from 1 to 6 carbons, unless otherwise specified. Alkyl groups are exemplified by methyl, ethyl, n- and iso-propyl, n-, sec-, iso- and tert-butyl, neopentyl, and the like, and may be optionally substituted with one, two, three, or, in the case of alkyl groups of two carbons or more, four substituents independently selected from the group consisting of: (1) $C_{1-6}$ alkoxy; (2) $C_{1-6}$ alkylsulfinyl; (3) amino; (4) $C_{6-10}$ aryl-$C_{1-6}$ alkoxy; (5) azido; (6) halo; (7) ($C_{2-9}$heterocyclyl)oxy; (8) hydroxy; (9) nitro; (10) oxo (e.g., carboxyaldehyde or acyl); (11) $C_{1-7}$ spirocyclyl; (12) thioalkoxy; (13) thiol; (14) —$CO_2R^{A'}$, where $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (15) —C(O)$NR^{B'}R^{C'}$, where each of $R^{B'}$ and $R^{C'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (16) —$SO_2R^{D'}$, where $R^{D'}$ is selected from the group consisting of (a) $C_{1-6}$ alkyl, (b) $C_{6-10}$ aryl, and (c) $C_{1-6}$ alk-$C_{6-10}$ aryl; and (17) —$SO_2NR^{E'}R^{F'}$, where each of $R^{E'}$ and $R^{F'}$ is, independently, selected from the group consisting of (a) hydrogen, (b) $C_{1-6}$ alkyl, (c) $C_{6-10}$ aryl and (d) $C_{1-6}$ alk-$C_{6-10}$ aryl. In some embodiments, each of these groups can be further substituted as described herein. For example, the alkylene group of a $C_1$-alkaryl can be further substituted with an oxo group to afford the respective aryloyl substituent.

The term "alkylene" and the prefix "alk-," as used herein, represent a saturated divalent hydrocarbon group derived from a straight or branched chain saturated hydrocarbon by the removal of two hydrogen atoms, and is exemplified by methylene, ethylene, isopropylene, and the like. The term "$C_{x-y}$ alkylene" and the prefix "$C_{x-y}$ alk-" represent alkylene groups having between x and y carbons. Exemplary values for x are 1, 2, 3, 4, 5, and 6, and exemplary values for y are 2, 3, 4, 5, 6, 7, 8, 9, or 10. In some embodiments, the alkylene can be further substituted with 1, 2, 3, or 4 substituent groups as defined herein for an alkyl group.

The term "alkylsulfinyl," as used herein, represents an alkyl group attached to the parent molecular group through an —S(O)— group. Exemplary unsubstituted alkylsulfinyl groups are from 1 to 6 carbons. In some embodiments, the alkyl group can be further substituted with 1, 2, 3, or 4 substituent groups as defined herein.

The term "alkylsulfinylalkyl," as used herein, represents an alkyl group, as defined herein, substituted by an alkylsulfinyl group. Exemplary unsubstituted alkylsulfinylalkyl groups are from 2 to 12 carbons. In some embodiments, each alkyl group can be further substituted with 1, 2, 3, or 4 substituent groups as defined herein.

The term "alkynyl," as used herein, represents monovalent straight or branched chain groups from two to six carbon atoms containing a carbon-carbon triple bond and is exemplified by ethynyl, 1-propynyl, and the like. Alkynyl groups may be optionally substituted with 1, 2, 3, or 4 substituent groups that are selected, independently, from aryl, cycloalkyl, or heterocyclyl (e.g., heteroaryl), as defined herein, or any of the exemplary alkyl substituent groups described herein.

The term "alkynyloxy" represents a chemical substituent of formula —OR, where R is a $C_{2-6}$ alkynyl group, unless otherwise specified. In some embodiments, the alkynyl group can be further substituted with 1, 2, 3, or 4 substituent groups as defined herein.

The term "amino," as used herein, represents $N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkenyl, alkynyl, alkoxy, aryl, alkaryl, cycloalkyl, alkcycloalkyl, heterocyclyl (e.g., heteroaryl), alkheterocyclyl (e.g., alkheteroaryl), or two $R^{N1}$ combine to form a heterocyclyl or an N-protecting group, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$). In a preferred embodiment, amino is —$NH_2$ or —$NHR^{N1}$, wherein $R^{N1}$ is, independently, OH, $NO_2$, $NH_2$, $NR^{N2}_2$, $SO_2OR^{N2}$, $SO_2R^{N2}$, $SOR^{N2}$, alkyl, or aryl, and each $R^{N2}$ can be H, $C_{1-6}$ alkyl, or $C_{6-10}$ aryl.

The term "aminoalkyl," as used herein, represents an alkyl group, as defined herein, substituted by an amino group, as defined herein. The alkyl and amino each can be further substituted with 1, 2, 3, or 4 substituent groups as described herein for the respective group.

The term "aryl," as used herein, represents a mono-, bicyclic, or multicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with 1, 2, 3, 4, or 5 substituents independently selected from the group consisting of: (1) $C_{1-7}$ acyl (e.g., carboxyaldehyde); (2) $C_{1-6}$ alkyl (e.g., $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-6}$ alkoxy (e.g., perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-6}$ thioalkoxy; (17) —$(CH_2)_qCO_2R^{A'}$, where q is an integer from zero to four, and $R^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) $(CH_2)_qCONR^{B'}R^{C'}$, where q is an integer from zero to four and where $R^{B'}$ and $R^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —$(CH_2)_qSO_2R^{D'}$, where q is an integer from zero to four and where $R^{D'}$ is selected from the group consisting of (a) alkyl, (b) $C_{6-10}$ aryl, and (c) alk-$C_{6-10}$ aryl; (20) —$(CH_2)_qSO_2NR^{E'}R^{F'}$, where q is an integer from zero to four and where each of $R^{E'}$ and $R^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; and (25) $C_{1-6}$ alk-$C_{1-12}$ heterocyclyl (e.g., $C_{1-6}$ alk-$C_{1-12}$ heteroaryl). In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "arylalkoxy," as used herein, represents an alkaryl group, as defined herein, attached to the parent molecular group through an oxygen atom. Exemplary unsubstituted arylalkoxy groups are from 7 to 16 carbons (e.g., $C_{6-10}$ aryl-$C_{1-6}$ alkoxy). In some embodiments, the alkaryl group can be substituted with 1, 2, 3, or 4 substituents as defined herein.

The term "aryloxy" represents a chemical substituent of formula OR', where R' is an aryl group of 6 to 18 carbons, unless otherwise specified. In some embodiments, the aryl group can be substituted with 1, 2, 3, or 4 substituents as defined herein.

The term "aryloyl," as used herein, represents an aryl group, as defined herein, that is attached to the parent molecular group through a carbonyl group. Exemplary unsubstituted aryloyl groups are of 7 to 11 carbons. In some embodiments, the aryl group can be substituted with 1, 2, 3, or 4 substituents as defined herein.

The term "azido" represents an $N_3$ group, which can also be represented as —N=N=N.

The term "bicyclic," as used herein, refer to a structure having two rings, which may be aromatic or non-aromatic. Bicyclic structures include spirocyclyl groups, as defined herein, and two rings that share one or more bridges, where such bridges can include one atom or a chain including two, three, or more atoms. Exemplary bicyclic groups include a bicyclic carbocyclyl group, where the first and second rings are carbocyclyl groups, as defined herein; a bicyclic aryl groups, where the first and second rings are aryl groups, as defined herein; bicyclic heterocyclyl groups, where the first ring is a heterocyclyl group and the second ring is a carbocyclyl (e.g., aryl) or heterocyclyl (e.g., heteroaryl) group; and bicyclic heteroaryl groups, where the first ring is a heteroaryl group and the second ring is a carbocyclyl (e.g., aryl) or heterocyclyl (e.g., heteroaryl) group. In some embodiments, the bicyclic group can be substituted with 1, 2, 3, or 4 substituents as defined herein for cycloalkyl, heterocyclyl, and aryl groups.

The terms "carbocyclic" and "carbocyclyl," as used herein, refer to an optionally substituted $C_{3-12}$ monocyclic, bicyclic, or tricyclic structure in which the rings, which may be aromatic or non-aromatic, are formed by carbon atoms. Carbocyclic structures include cycloalkyl, cycloalkenyl, and aryl groups.

As used herein, the term "carbamyl" refers to a carbamate group having the structure —$NR^{N1}C(=O)OR$ or —$OC(=O)N(R^{N1})_2$, where the meaning of each $R^{N1}$ is found in the definition of "amino" provided herein, and R is alkyl, cycloalkyl, alkcycloalkyl, aryl, alkaryl, heterocyclyl (e.g., heteroaryl), or alkheterocyclyl (e.g., alkheteroaryl), as defined herein.

The term "carbonyl," as used herein, represents a C(O) group, which can also be represented as C=O.

The term "carboxyaldehyde" represents an acyl group having the structure CHO.

The term "carboxyl," as used herein, means —CO$_2$H.

The term "cyano," as used herein, represents an —CN group.

The term "cycloalkyl," as used herein represents a monovalent saturated or unsaturated non-aromatic cyclic hydrocarbon group from three to eight carbons, unless otherwise specified, and is exemplified by cyclopropyl, cyclobutyl, cyclopentyl, cyclohexyl, cycloheptyl, bicyclo[2.2.1.]heptyl, and the like. When the cycloalkyl group includes one carbon-carbon double bond, the cycloalkyl group can be referred to as a "cycloalkenyl" group. Exemplary cycloalkenyl groups include cyclopentenyl, cyclohexenyl, and the like. The cycloalkyl groups of this invention can be optionally substituted with: (1) $C_{1-7}$ acyl (e.g., carboxyaldehyde); (2) $C_{1-6}$ alkyl (e.g., $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-6}$ alkoxy (e.g., perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{1-12}$ heteroaryl); (13) ($C_{1-12}$ heterocyclyl)oxy; (14) hydroxy; (15) nitro; (16) $C_{1-6}$ thioalkoxy; (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{6-10}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{6-10}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{6-10}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) $C_{6-10}$ aryl-$C_{1-6}$ alkoxy; (25) $C_{1-6}$ alk-$C_{1-12}$ heterocyclyl (e.g., $C_{1-6}$ alk-$C_{1-12}$ heteroaryl); and (26) oxo. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "cycloalkoxy," as used herein, represents a cycloalkyl group, as defined herein, attached to the parent molecular group through an oxygen atom. Exemplary unsubstituted cycloalkoxy groups are from 3 to 8 carbons. In some embodiment, the cycloalkyl group can be further substituted with 1, 2, 3, or 4 substituent groups as described herein.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "halo," as used herein, represents a halogen selected from bromine, chlorine, iodine, or fluorine.

The term "haloalkoxy," as used herein, represents an alkoxy group, as defined herein, substituted by a halogen group (i.e., F, Cl, Br, or I). A haloalkoxy may be substituted with one, two, three, or, in the case of alkyl groups of two carbons or more, four halogens. Haloalkoxy groups include perfluoroalkoxys (e.g., —OCF$_3$), —OCHF$_2$, —OCH$_2$F, —OCCl$_3$, —OCH$_2$CH$_2$Br, —OCH$_2$CH(CH$_2$CH$_2$Br)CH$_3$, and —OCHICH$_3$. In some embodiments, the haloalkoxy group can be further substituted with 1, 2, 3, or 4 substituent groups as described herein for alkyl groups.

The term "haloalkyl," as used herein, represents an alkyl group, as defined herein, substituted by a halogen group (i.e., F, Cl, Br, or I). A haloalkyl may be substituted with one, two, three, or, in the case of alkyl groups of two carbons or more, four halogens. Haloalkyl groups include perfluoroalkyls (e.g., —CF$_3$), —CHF$_2$, —CH$_2$F, —CCl$_3$, —CH$_2$CH$_2$Br, —CH$_2$CH(CH$_2$CH$_2$Br)CH$_3$, and —CHICH$_3$. In some embodiments, the haloalkyl group can be further substituted with 1, 2, 3, or 4 substituent groups as described herein for alkyl groups.

The term "heteroalkylene," as used herein, refers to an alkylene group, as defined herein, in which one or two of the constituent carbon atoms have each been replaced by nitrogen, oxygen, and sulfur. In some embodiments, the heteroalkylene group can be further substituted with 1, 2, 3, or 4 substituent groups as described herein for alkylene groups.

The term "heteroaryl," as used herein, represents that subset of heterocyclyls, as defined herein, which are aromatic: i.e., they contain 4n+2 pi electrons within the mono- or multicyclic ring system. Exemplary unsubstituted heteroaryl groups are of 1 to 12 (e.g., 1 to 11, 1 to 10, 1 to 9, 2 to 12, 2 to 11, 2 to 10, or 2 to 9) carbons. In some embodiment, the heteroaryl is substituted with 1, 2, 3, or 4 substituents groups as defined for a heterocyclyl group.

The term "heterocyclyl," as used herein represents a 5-, 6- or 7-membered ring, unless otherwise specified, containing one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocyclyl groups are of 1 to 12 (e.g., 1 to 11, 1 to 10, 1 to 9, 2 to 12, 2 to 11, 2 to 10, or 2 to 9) carbons. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, indazolyl, quinolyl, isoquinolyl, quinoxalinyl, dihydroquinoxalinyl, quinazolinyl, cinnolinyl, phthalazinyl, benzimidazolyl, benzothiazolyl, benzoxazolyl, benzothiadiazolyl, furyl, thienyl, thiazolidinyl, isothiazolyl, triazolyl, tetrazolyl, oxadiazolyl (e.g., 1,2,3-oxadiazolyl), purinyl, thiadiazolyl (e.g., 1,2, 3-thiadiazolyl), tetrahydrofuranyl, dihydrofuranyl, tetrahydrothienyl, dihydrothienyl, dihydroindolyl, dihydroquinolyl, tetrahydroquinolyl, tetrahydroisoquinolyl, dihydroisoquinolyl, pyranyl, dihydropyranyl, dithiazolyl, benzofuranyl, isobenzofuranyl, benzothienyl, and the like, including dihydro and tetrahydro forms thereof, where one or more double bonds are reduced and replaced with hydrogens. Still other exemplary heterocyclyls include: 2,3,4,5-tetrahydro-2-oxo-oxazolyl; 2,3-dihydro-2-oxo-1H-imidazolyl; 2,3, 4,5-tetrahydro-5-oxo-1H-pyrazolyl (e.g., 2,3,4,5-tetrahydro-2-phenyl-5-oxo-1H-pyrazolyl); 2,3,4,5-tetrahydro-2,4-dioxo-1H-imidazolyl (e.g., 2,3,4,5-tetrahydro-2,4-dioxo-5-methyl-5-phenyl-1H-imidazolyl); 2,3-dihydro-2-thioxo-1,3, 4-oxadiazolyl (e.g., 2,3-dihydro-2-thioxo-5-phenyl-1,3,4-oxadiazolyl); 4,5-dihydro-5-oxo-1H-triazolyl (e.g., 4,5-dihydro-3-methyl-4-amino 5-oxo-1H-triazolyl); 1,2,3,4-tetrahydro-2,4-dioxopyridinyl (e.g., 1,2,3,4-tetrahydro-2,4-dioxo-3,3-diethylpyridinyl); 2,6-dioxo-piperidinyl (e.g., 2,6-dioxo-3-ethyl-3-phenylpiperidinyl); 1,6-dihydro-6-oxopyridiminyl; 1,6-dihydro-4-oxopyrimidinyl (e.g., 2-(methylthio)-1,6-dihydro-4-oxo-5-methylpyrimidin-1-yl); 1,2,3,4-tetrahydro-2,4-dioxopyrimidinyl (e.g., 1,2,3,4-tetrahydro-2,4-dioxo-3-ethylpyrimidinyl); 1,6-dihydro-6-oxopyridazinyl (e.g., 1,6-dihydro-6-oxo-3-ethylpyridazinyl); 1,6-dihydro-6-oxo-1,2,4-triazinyl (e.g., 1,6-dihydro-5-isopropyl-6-oxo-1,2,4-triazinyl); 2,3-dihydro-2-oxo-1H-indolyl (e.g., 3,3-dimethyl-2,3-dihydro-2-oxo-1H-indolyl and 2,3-dihydro-2-oxo-3,3'-spiropropane-1H-indol-1-yl); 1,3-dihydro-1-oxo-2H-iso-indolyl; 1,3-dihydro-1,3-dioxo-2H-iso-indolyl; 1H-benzopyrazolyl (e.g., 1-(ethoxycarbonyl)-1H-benzopyrazolyl); 2,3-dihydro-2-oxo-1H-benzimidazolyl (e.g., 3-ethyl-2,3-dihydro-2-oxo-1H-benzimidazolyl); 2,3-dihydro-2-oxo-benzoxazolyl (e.g., 5-chloro-2,3-dihydro-2-oxo-benzoxazolyl); 2,3-dihydro-2-oxo-benzoxazolyl; 2-oxo-2H-benzopyranyl; 1,4-benzodioxanyl; 1,3-benzodioxanyl; 2,3-dihydro-3-oxo, 4H-1,3-benzothiazinyl; 3,4-dihydro-4-oxo-3H-quinazolinyl (e.g., 2-methyl-3,4-dihydro-4-oxo-3H-quinazolinyl); 1,2,3,4-tetrahydro-2,4-dioxo-3H-quinazolyl (e.g., 1-ethyl-1,2,3,4-tetrahydro-2,4-dioxo-3H-quinazolyl); 1,2,3,6-tetrahydro-2,6-dioxo-7H-purinyl (e.g., 1,2,3,6-tetrahydro-1,3-dimethyl-2,6-dioxo-7H-purinyl); 1,2, 3,6-tetrahydro-2,6-dioxo-1H-purinyl (e.g., 1,2,3,6-tetrahydro-3,7-dimethyl-2,6-dioxo-1H-purinyl); 2-oxobenz[c,d]indolyl; 1,1-dioxo-2H-naphth[1,8-c,d]isothiazolyl; and 1,8-naphthylenedicarboxamido. Additional heterocyclics include 3,3a,4,5,6,6a-hexahydro-pyrrolo[3,4-b]pyrrol-(2H)-yl, and 2,5-diazabicyclo[2.2.1]heptan-2-yl, homopiperazinyl (or diazepanyl), tetrahydropyranyl, dithiazolyl, benzofuranyl, benzothienyl, oxepanyl, thiepanyl, azocanyl, oxecanyl, and thiocanyl. Heterocyclic groups also include groups of the formula

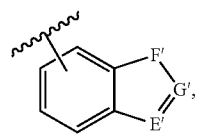

where

E' is selected from the group consisting of —N— and —CH—; F' is selected from the group consisting of —N═CH—, —NH—CH$_2$—, —NH—C(O)—, —NH—, —CH═N—, —CH$_2$—NH—, —C(O)—NH—, —CH═CH—, —CH$_2$—, —CH$_2$CH$_2$—, —CH$_2$O—, —OCH$_2$—, —O—, and —S—; and G' is selected from the group consisting of —CH— and —N—. Any of the heterocyclyl groups mentioned herein may be optionally substituted with one, two, three, four or five substituents independently selected from the group consisting of: (1) $C_{1-7}$ acyl (e.g., carboxyaldehyde); (2) $C_{1-6}$ alkyl (e.g., $C_{1-6}$ alkoxy-$C_{1-6}$ alkyl, $C_{1-6}$ alkylsulfinyl-$C_{1-6}$ alkyl, amino-$C_{1-6}$ alkyl, azido-$C_{1-6}$ alkyl, (carboxyaldehyde)-$C_{1-6}$ alkyl, halo-$C_{1-6}$ alkyl (e.g., perfluoroalkyl), hydroxy-$C_{1-6}$ alkyl, nitro-$C_{1-6}$ alkyl, or $C_{1-6}$ thioalkoxy-$C_{1-6}$ alkyl); (3) $C_{1-6}$ alkoxy (e.g., perfluoroalkoxy); (4) $C_{1-6}$ alkylsulfinyl; (5) $C_{6-10}$ aryl; (6) amino; (7) $C_{1-6}$ alk-$C_{6-10}$ aryl; (8) azido; (9) $C_{3-8}$ cycloalkyl; (10) $C_{1-6}$ alk-$C_{3-8}$ cycloalkyl; (11) halo; (12) $C_{1-12}$ heterocyclyl (e.g., $C_{2-12}$ heteroaryl); (13) ($C_{1-12}$ heterocyclyl)oxy; (14) hydroxy; (15) nitro; (16) $C_{1-6}$ thioalkoxy; (17) —(CH$_2$)$_q$CO$_2$R$^{A'}$, where q is an integer from zero to four, and R$^{A'}$ is selected from the group consisting of (a) $C_{1-6}$ alkyl, (b) $C_{6-10}$ aryl, (c) hydrogen, and (d) $C_{1-6}$ alk-$C_{6-10}$ aryl; (18) —(CH$_2$)$_q$CONR$^{B'}$R$^{C'}$, where q is an integer from zero to four and where R$^{B'}$ and R$^{C'}$ are independently selected from the group consisting of (a) hydrogen, (b) $C_{1-6}$ alkyl, (c) $C_{6-10}$ aryl, and (d) $C_{1-6}$ alk-$C_{6-10}$ aryl; (19) —(CH$_2$)$_q$SO$_2$R$^{D'}$, where q is an integer from zero to four and where R$^{D'}$ is selected from the group consisting of (a) $C_{1-6}$ alkyl, (b) $C_{6-10}$ aryl, and (c) $C_{1-6}$ alk-$C_{6-10}$ aryl; (20) —(CH$_2$)$_q$SO$_2$NR$^{E'}$R$^{F'}$, where q is an integer from zero to four and where each of R$^{E'}$ and R$^{F'}$ is, independently, selected from the group consisting of (a) hydrogen, (b) $C_{1-6}$ alkyl, (c) $C_{6-10}$ aryl, and (d) $C_{1-6}$ alk-$C_{6-10}$ aryl; (21) thiol; (22) $C_{6-10}$ aryloxy; (23) $C_{3-8}$ cycloalkoxy; (24) arylalkoxy; (25) $C_{1-6}$ alk-$C_{1-12}$ heterocyclyl (e.g., $C_{1-6}$ alk-$C_{1-12}$ heteroaryl); (26) oxo; and (27) ($C_{1-12}$ heterocyclyl)imino. In some embodiments, each of these groups can be further substituted as described herein. For example, the alkylene group of a $C_1$-alkaryl or a $C_1$-alkheterocyclyl can be further substituted with an oxo group to afford the respective aryloyl and (heterocyclyl)oyl substituent group.

The term "(heterocyclyl)imino," as used herein, represents a heterocyclyl group, as defined herein, attached to the parent molecular group through an imino group. In some embodiments, the heterocyclyl group can be substituted with 1, 2, 3, or 4 substituent groups as defined herein.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "(heterocyclyl)oyl," as used herein, represents a heterocyclyl group, as defined herein, attached to the parent molecular group through a carbonyl group. In some embodiments, the heterocyclyl group can be substituted with 1, 2, 3, or 4 substituent groups as defined herein.

The term "hydrocarbon," as used herein, represents a group consisting only of carbon and hydrogen atoms.

The term "hydroxy," as used herein, represents an OH group.

The term "hydroxyalkyl," as used herein, represents an alkyl group, as defined herein, substituted by one to three hydroxy groups, with the proviso that no more than one hydroxy group may be attached to a single carbon atom of the alkyl group, and is exemplified by hydroxymethyl, dihydroxypropyl, and the like.

The term "isomer," as used herein, means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The term "N-protected amino," as used herein, refers to an amino group, as defined herein, to which is attached one or two N-protecting groups, as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical. Perfluoroalkoxy groups are exemplified by trifluoromethoxy, pentafluoroethoxy, and the like.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutically acceptable prodrugs," as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharm. Sci.* 66(1):1-19, 1977 and in *Pharmaceutical Salts: Properties, Selection, and Use*, P. H. Stahl and C. G. Wermuth (eds.), Wiley-VCH, 2008. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The terms "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

The term "prodrug," as used herein, represents compounds that are rapidly transformed in vivo to the parent compound of the above formula, for example, by hydrolysis in blood. Prodrugs of the compounds of the invention may be conventional esters. Some common esters that have been utilized as prodrugs are phenyl esters, aliphatic ($C_{1-8}$ or $C_{8-24}$) esters, cholesterol esters, acyloxymethyl esters, carbamates, and amino acid esters. For example, a compound of the invention that contains an OH group may be acylated at this position in its prodrug form. A thorough discussion is provided in T. Higuchi and V. Stella, "Pro-drugs as Novel Delivery Systems," in: Bioreversible Carriers in Drug Design, A.C.S. Symposium Series, Edward B. Roche (ed.), American Pharmaceutical Association and Pergamon Press, 1987, vol. 14; and Judkins et al., Synth. Commun. 26(23):4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

The term "spirocyclyl," as used herein, represents a $C_{2-7}$ alkylene diradical, both ends of which are bonded to the same carbon atom of the parent group to form a spirocyclic group, and also a $C_{1-6}$ heteroalkylene diradical, both ends of which are bonded to the same atom. The heteroalkylene radical forming the spirocyclyl group can containing one, two, three, or four heteroatoms independently selected from the group consisting of nitrogen, oxygen, and sulfur. In some embodiments, the spirocyclyl group includes one to seven carbons, excluding the carbon atom to which the diradical is attached. The spirocyclyl groups of the invention may be optionally substituted with 1, 2, 3, or 4 substituents provided herein as optional substituents for cycloalkyl and/or heterocyclyl groups.

The term "stereoisomer," as used herein, refers to all possible different isomeric as well as conformational forms which a compound may possess (e.g., a compound of any formula described herein, such as formulas (I), (I-2), (Ia), (Ia-2), (Ib), (Ib-2), (IIa), (IIa-2), (IIb), and (IIb-2)), in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The term "sulfonyl," as used herein, represents an —$S(O)_2$— group.

The term "thioalkaryl," as used herein, represents a chemical substituent of formula SR, where R is an alkaryl group. In some embodiments, the alkaryl group can be further substituted with 1, 2, 3, or 4 substituent groups as described herein.

The term "thioalkheterocyclyl," as used herein, represents a chemical substituent of formula —SR, where R is an alkheterocyclyl group. In some embodiments, the alkheterocyclyl group can be further substituted with 1, 2, 3, or 4 substituent groups as described herein.

The term "thioalkoxy," as used herein, represents a chemical substituent of formula —SR, where R is an alkyl group. In some embodiments, the alkyl group can be further substituted with 1, 2, 3, or 4 substituent groups as described herein.

The term "thiol" represents an —SH group.

As used herein, and as well understood in the art, "treatment" is an approach for obtaining beneficial or desired results, for example, clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; remission (whether partial or total), whether detectable or undetectable; and improvement of a disease, disorder, or condition by employing an agent (e.g., a compound of the invention) in combination with another specific agent or therapy directed toward treating the disease, disorder, or condition. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. "Prophylactically treating" a disease, disorder, or condition means that treatment is provided to the subject prior to the onset of symptoms of the disease, disorder, or condition.

Other features and advantages of the invention will be apparent from the following detailed description, the drawings, and the claims.

BRIEF DESCRIPTION OF THE DRAWINGS

In FIG. 1B, inset tables provide data for each peak [#] in the following order: retention time (in minutes, min), type, width (in minutes, min), area, height, and area (in %).

In FIG. 3B, inset tables provide data for each peak [#] in the following order: retention time (in minutes, min), type, width (in minutes, min), area, height, and area (in %).

DETAILED DESCRIPTION

Figure 1A:
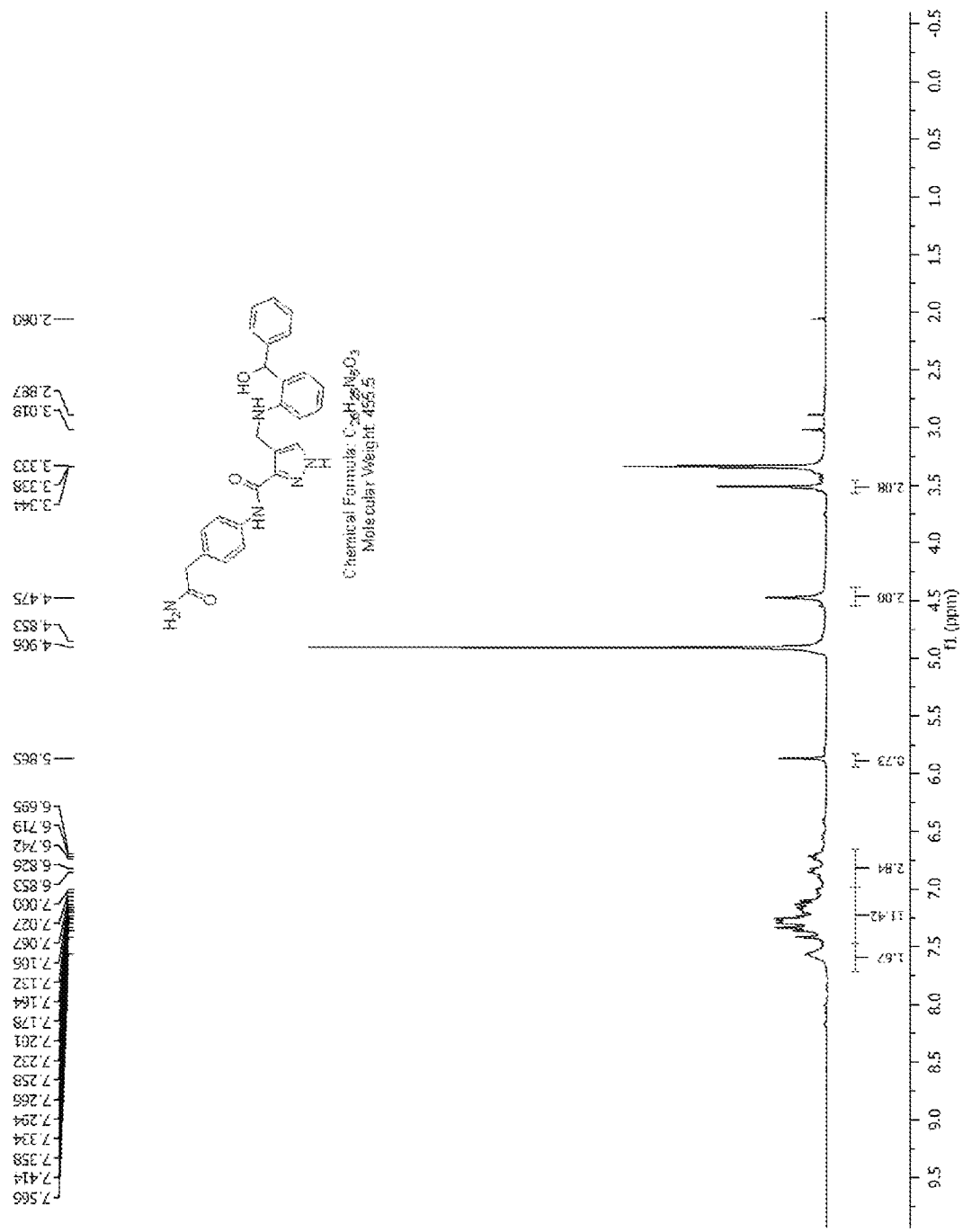
FIGS. 1A-1C are spectra for compound 1, including those for NMR (FIG. 1A), LC-MS (FIG. 1B), and MS (FIG. 1C) spectroscopy.

The invention features novel benzhydrol-pyrazole derivatives of formulas (I), (I-2), (Ia), (Ia-2), (Ib), (Ib-2), (IIa), (IIa-2), (IIb), and (IIb-2), and related compounds, having kinase (e.g., BTK) inhibitory activity, pharmaceutical and diagnostic compositions containing them, and their medical uses. Exemplary compounds of the invention are shown in Table 1, including stereoisomers (e.g., diastereomers or enantiomers), pharmaceutically acceptable salts, or pharmaceutically acceptable prodrugs thereof.

TABLE 1

| No. | Structure | Name |
|---|---|---|
| 1 | 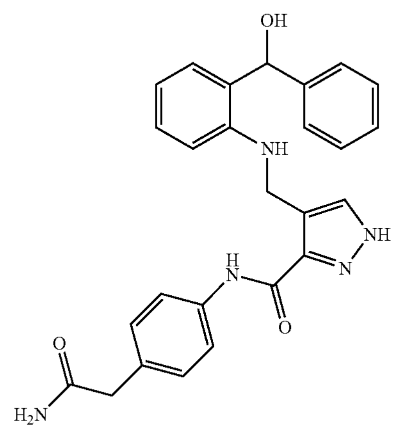 [SMILES: NC(=O)Cc1ccc(NC(=O)c2n[nH]cc2CNc2ccccc2C(O)c2ccccc2)cc1] | N-(4-(2-amino-2-oxoethyl)phenyl)-4-(((2-(hydroxy(phenyl)methyl)phenyl)amino)methyl)-1H-pyrazole-3-carboxamide |
| 2 | 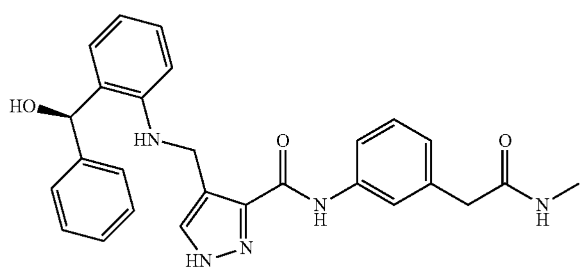 [SMILES: CNC(=O)Cc1cccc(NC(=O)c2n[nH]cc2CNc2ccccc2[C@H](O)c2ccccc2)c1] | (R)-4-(((2-(hydroxy(phenyl)methyl)phenyl)amino)methyl)-N-(3-(2-(methylamino)-2-oxoethyl)phenyl)-1H-pyrazole-3-carboxamide |
| 3 | 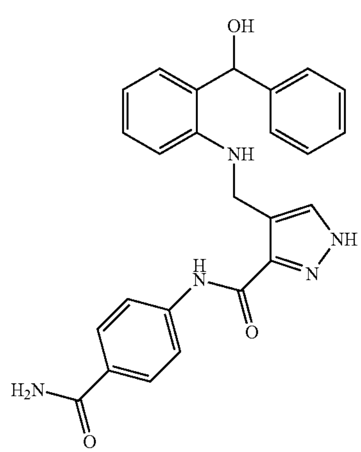 [SMILES: NC(=O)c1ccc(NC(=O)c2n[nH]cc2CNc2ccccc2C(O)c2ccccc2)cc1] | N-(4-carbamoylphenyl)-4-(((2-(hydroxy(phenyl)methyl)phenyl)amino)methyl)-1H-pyrazole-3-carboxamide |

TABLE 1-continued

| No. | Structure | Name |
|---|---|---|
| 4 | 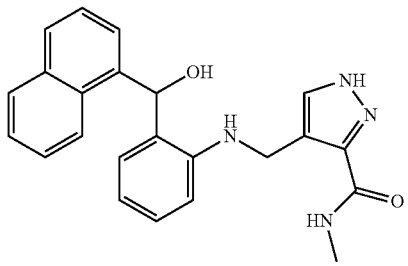 [SMILES: CNC(=O)c1n[nH]cc1CNc1ccccc1C(O)c1cccc2ccccc12] | 4-(((2-(hydroxy(naphthalen-1-yl)methyl)phenyl)amino)methyl)-N-methyl-1H-pyrazole-3-carboxamide |
| 5 | 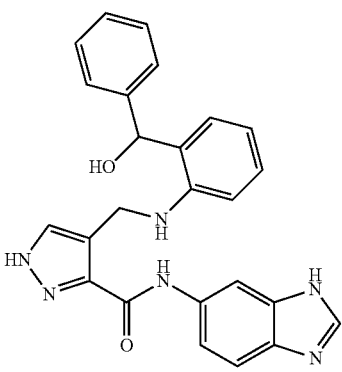 [SMILES: O=C(Nc1ccc2nc[nH]c2c1)c1n[nH]cc1CNc1ccccc1C(O)c1ccccc1] | N-(1H-benzo[d]imidazol-6-yl)-4-(((2-(hydroxy(phenyl)methyl)phenyl)amino)methyl)-1H-pyrazole-3-carboxamide |
| 6 | 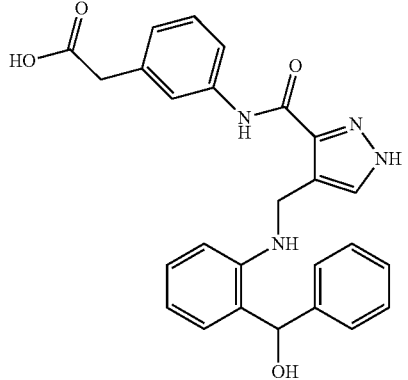 [SMILES: O=C(O)Cc1cccc(NC(=O)c2n[nH]cc2CNc2ccccc2C(O)c2ccccc2)c1] | 2-(3-(4-(((2-(hydroxy(phenyl)methyl)phenyl)amino)methyl)-1H-pyrazole-3-carboxamido)phenyl)acetic acid |
| 7 | 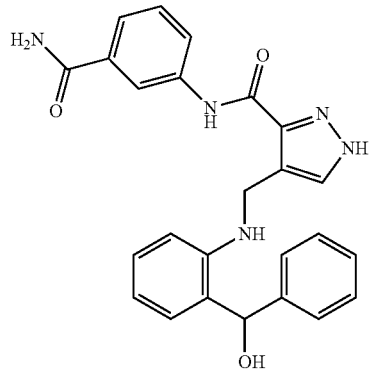 [SMILES: NC(=O)c1cccc(NC(=O)c2n[nH]cc2CNc2ccccc2C(O)c2ccccc2)c1] | N-(3-carbamoylphenyl)-4-(((2-(hydroxy(phenyl)methyl)phenyl)amino)methyl)-1H-pyrazole-3-carboxamide |

TABLE 1-continued

| No. | Structure | Name |
|---|---|---|
| 8 | 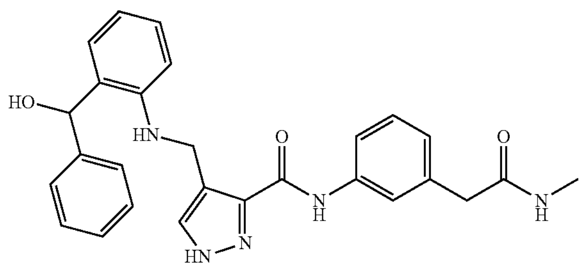 [SMILES: CNC(=O)Cc1cccc(NC(=O)c2n[nH]cc2CNc2ccccc2C(O)c2ccccc2)c1] | 4-(((2-(hydroxy(phenyl)methyl)phenyl)amino)methyl)-N-(3-(2-(methylamino)-2-oxoethyl)phenyl)-1H-pyrazole-3-carboxamide |
| 9 | 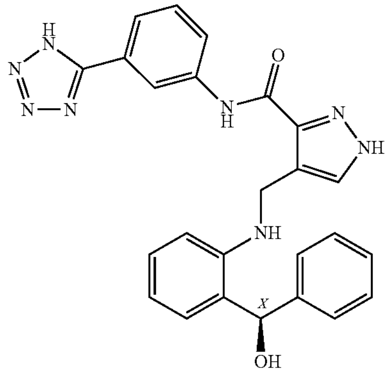 | (R)-N-(3-(1H-tetrazol-5-yl)phenyl)-4-(((2-(hydroxy(phenyl)methyl)phenyl)amino)methyl)-1H-pyrazole-3-carboxamide |
| 10 | 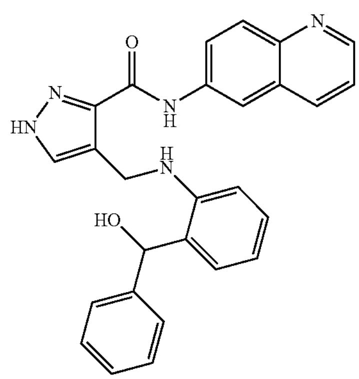 [SMILES: O=C(Nc1ccc2ncccc2c1)c1n[nH]cc1CNc1ccccc1C(O)c1ccccc1] | 4-(((2-(hydroxy(phenyl)methyl)phenyl)amino)methyl)-N-(quinolin-6-yl)-1H-pyrazole-3-carboxamide |
| 11 | 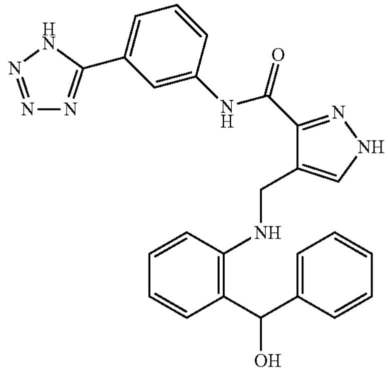 [SMILES: O=C(Nc1cccc(-c2nnn[nH]2)c1)c1n[nH]cc1CNc1ccccc1C(O)c1ccccc1] | N-(3-(1H-tetrazol-5-yl)phenyl)-4-(((2-(hydroxy(phenyl)methyl)phenyl)amino)methyl)-1H-pyrazole-3-carboxamide |

TABLE 1-continued

| No. | Structure | Name |
|---|---|---|
| 12 | 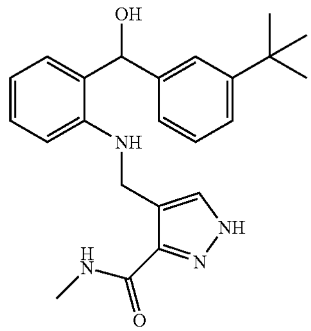 [SMILES: CNC(=O)c1n[nH]cc1CNc1ccccc1C(O)c1cccc(C(C)(C)C)c1] | 4-(((2-((3-(tert-butyl)phenyl)(hydroxy)methyl)phenyl)amino)methyl)-N-methyl-1H-pyrazole-3-carboxamide |
| 13 | 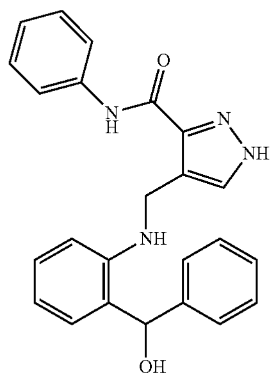 [SMILES: O=C(Nc1ccccc1)c1n[nH]cc1CNc1ccccc1C(O)c1ccccc1] | 4-(((2-(hydroxy(phenyl)methyl)phenyl)amino)methyl)-N-phenyl-1H-pyrazole-3-carboxamide |
| 14 | 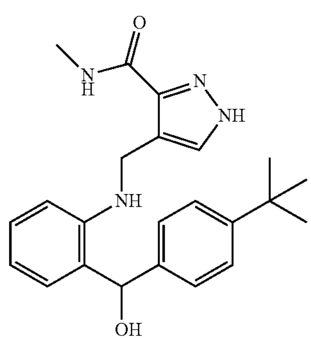 [SMILES: CNC(=O)c1n[nH]cc1CNc1ccccc1C(O)c1ccc(C(C)(C)C)cc1] | 4-(((2-((4-(tert-butyl)phenyl)(hydroxy)methyl)phenyl)amino)methyl)-N-methyl-1H-pyrazole-3-carboxamide |
| 15 | 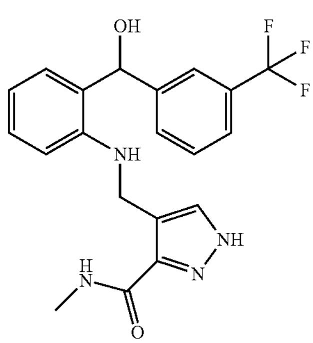 [SMILES: CNC(=O)c1n[nH]cc1CNc1ccccc1C(O)c1cccc(C(F)(F)F)c1] | 4-(((2-(hydroxy(3-(trifluoromethyl)phenyl)methyl)phenyl)amino)methyl)-N-methyl-1H-pyrazole-3-carboxamide |

TABLE 1-continued

| No. | Structure | Name |
|---|---|---|
| 16 | 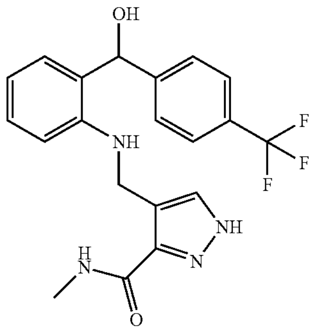 [SMILES: CNC(=O)c1n[nH]cc1CNc1ccccc1C(O)c1ccc(C(F)(F)F)cc1] | 4-(((2-(hydroxy(4-(trifluoromethyl)phenyl)methyl)phenyl)amino)methyl)-N-methyl-1H-pyrazole-3-carboxamide |
| 17 | 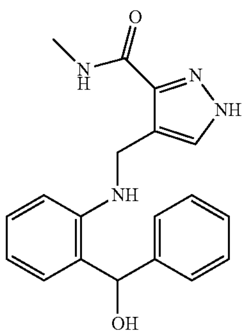 [SMILES: CNC(=O)c1n[nH]cc1CNc1ccccc1C(O)c1ccccc1] | 4-(((2-(hydroxy(phenyl)methyl)phenyl)amino)methyl)-N-methyl-1H-pyrazole-3-carboxamide |
| 18 | 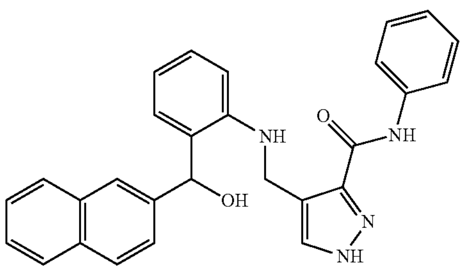 [SMILES: O=C(Nc1ccccc1)c1n[nH]cc1CNc1ccccc1C(O)c1ccc2ccccc2c1] | 4-(((2-(hydroxy(naphthalen-2-yl)methyl)phenyl)amino)methyl)-N-phenyl-1H-pyrazole-3-carboxamide |
| 19 | 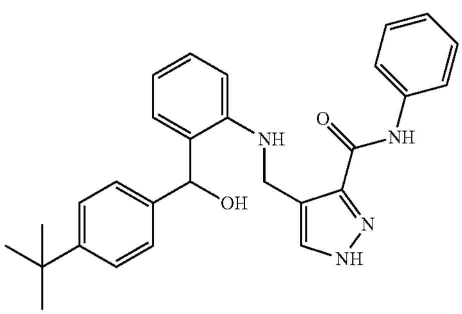 [SMILES: CC(C)(C)c1ccc(C(O)c2ccccc2NCc2c[nH]nc2C(=O)Nc2ccccc2)cc1] | 4-(((2-((4-(tert-butyl)phenyl)(hydroxy)methyl)phenyl)amino)methyl)-N-phenyl-1H-pyrazole-3-carboxamide |
| 20 | 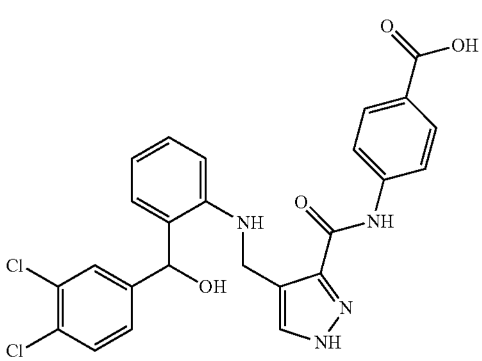 [SMILES: O=C(O)c1ccc(NC(=O)c2n[nH]cc2CNc2ccccc2C(O)c2ccc(Cl)c(Cl)c2)cc1] | (4-(4-(((2-(hydroxy(3,4-dichloro-phenyl)methyl)phenyl)amino)methyl)-1H-pyrazole-3-carboxamido)phenyl)carboxylic acid |

TABLE 1-continued

| No. | Structure | Name |
|---|---|---|
| 21 | 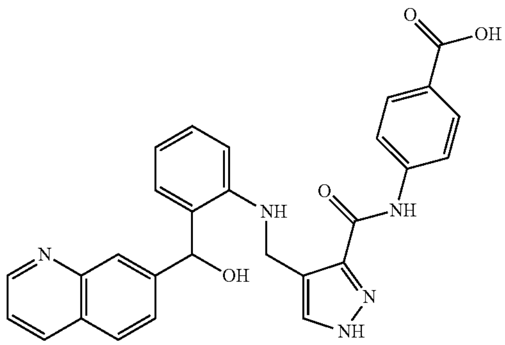 [SMILES: O=C(O)c1ccc(NC(=O)c2n[nH]cc2CNc2ccccc2C(O)c2ccc3cccnc3c2)cc1] | (4-(4-(((2-(hydroxy(7-quinolyl)methyl)phenyl)amino)methyl)-1H-pyrazole-3-carboxamido)phenyl)carboxylic acid |
| 22 | 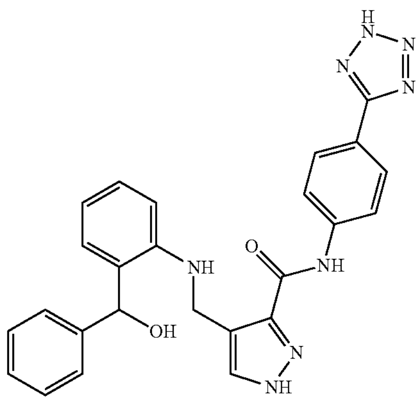 [SMILES: O=C(Nc1ccc(-c2nn[nH]n2)cc1)c1n[nH]cc1CNc1ccccc1C(O)c1ccccc1] | N-(4-(1H-tetrazol-4-yl)phenyl)-4-(((2-(hydroxy(phenyl)methyl)phenyl)amino)methyl)-1H-pyrazole-3-carboxamide |

Exemplary methods for synthesizing compounds of the invention are described herein.

Methods of Preparing Compounds of the Invention

The compounds of the invention can be prepared by processes analogous to those established in the art, for example, by the reaction sequences shown in Schemes 1-5. The numbering system used for the general schemes does not necessarily correspond to that employed elsewhere in the description or in the claims.

A compound of formula E-1 can be prepared under standard reductive conditions by treating a compound of formula C-1 with a compound of formula D-1, or suitable protected derivatives thereof, and "R" is H, hydroxy, alkyl, alkoxy, or any leaving group, such as chloro, bromo, iodo, or sulfonate (e.g., mesylate, tosylate, or triflate) (see Scheme 1). Exemplary reductive conditions include use of borohydride reagents (e.g., NaBH$_3$CN or NaBH$_4$) and any other useful conditions described herein.

Scheme 1

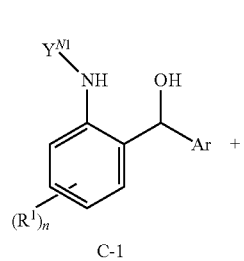

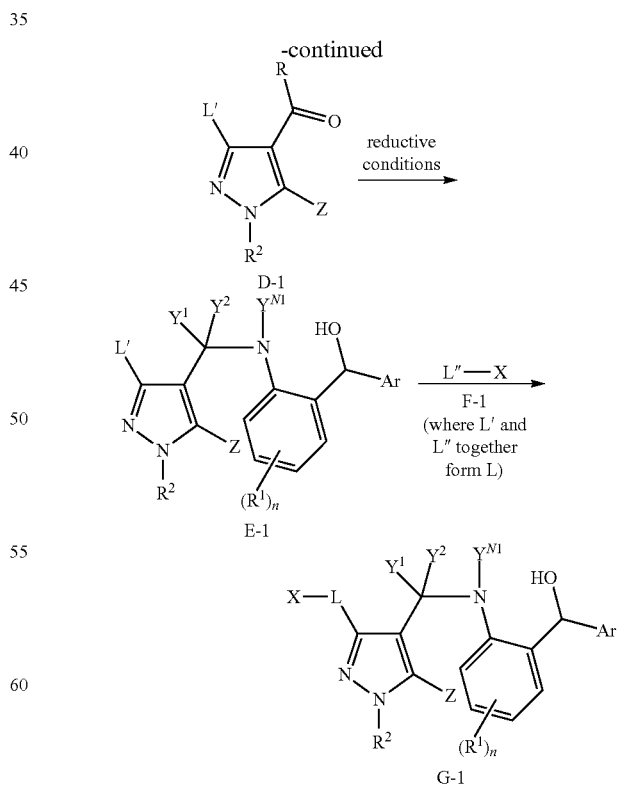

A compound of formula G-1 can be prepared by a coupling or acylation reaction between compounds of formulas E-1 and F-1, under standard conditions. For example, if E-1 and F-1 reacts to form an NH—C(O) moiety (e.g., where E-1 includes a carboxy and F-1 includes an amino, as defined herein, or vice versa), then any of the coupling reactions for peptides can be used (e.g., as described herein). Alternatively, if the compound of formula E-1 or F-1 includes an aldehyde or a ketone group, then reductive amination conditions can be used, such as a reducing agent (e.g., NaBH$_4$, NaBH(OAc)$_3$, NaCNBH$_4$, and the like, in an alcoholic solvent, such as ethanol) or the combination of a silane reagent (e.g., Et$_3$SiH, phenylsilanes (e.g., PhSiH$_3$), halosilanes (e.g., trichlorosilane), or silylsilanes (e.g., tris(trimethylsilyl)silane))) with catalytic InX$_3$, FeX$_3$, CuX, Ni[ligand]$_2$, PtX$_2$, Pd[ligand]$_2$, PdX$_2$[ligand]$_2$, or Ir[X(ligand)]$_2$, where each X is independently halo (e.g., bromo or chloro) and each ligand is any useful ligand (e.g., 1,5-cyclooctadiene, OAc, or PPh$_3$).

Alternatively, the compounds of the invention can be prepared by modifying the reactions of Scheme 1 in any useful manner. For example, a compound of formula E-2 can be prepared under standard conditions by treating a compound of formula C-2 with a compound of formula D-2, or suitable protected derivatives thereof, and "LG" is a leaving group, such as chloro, bromo, iodo, hydroxy, or sulfonate (e.g., mesylate, tosylate, or triflate) (see Scheme 2). A compound of formula G-2 can be prepared by a coupling or acylation reaction between compounds of formulas E-2 and F-2, under standard conditions, as discussed above for Scheme 1.

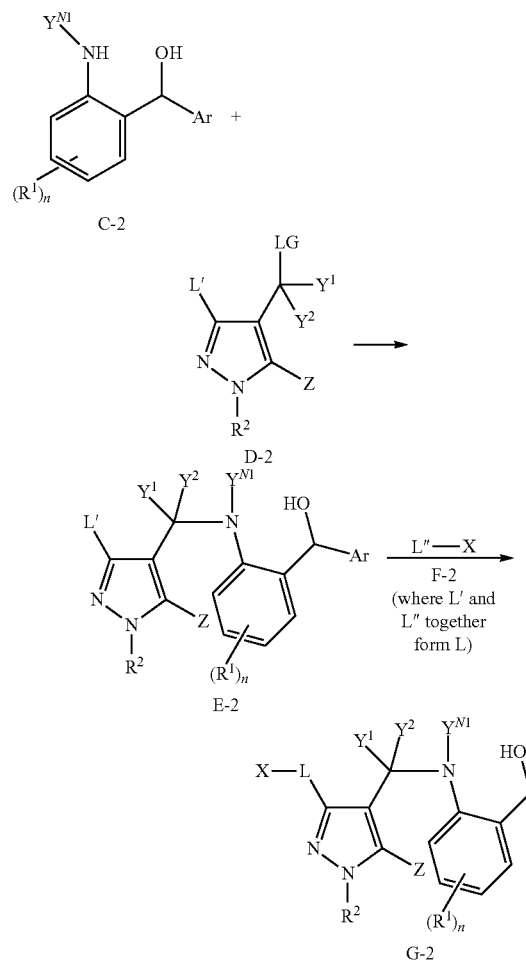

In addition, the compounds of the invention can be prepared by first reacting a pyrazolyl derivative with X, as described, e.g., in formula (I) or (Ia), and then reacting the pyrazolyl-X construct with the benzhydrol derivative core. For example, a compound of formula G-3 can be prepared under standard reductive conditions (e.g., any described herein) by treating a compound of formula C-3, or a suitable protected derivative thereof (e.g., an acetal derivative), with a compound of formula D-3, or a suitable protected derivative thereof, and "R" is H, hydroxy, alkyl, alkoxy, or any leaving group, such as chloro, bromo, iodo, or sulfonate (e.g., mesylate, tosylate, or triflate) (see Scheme 3).

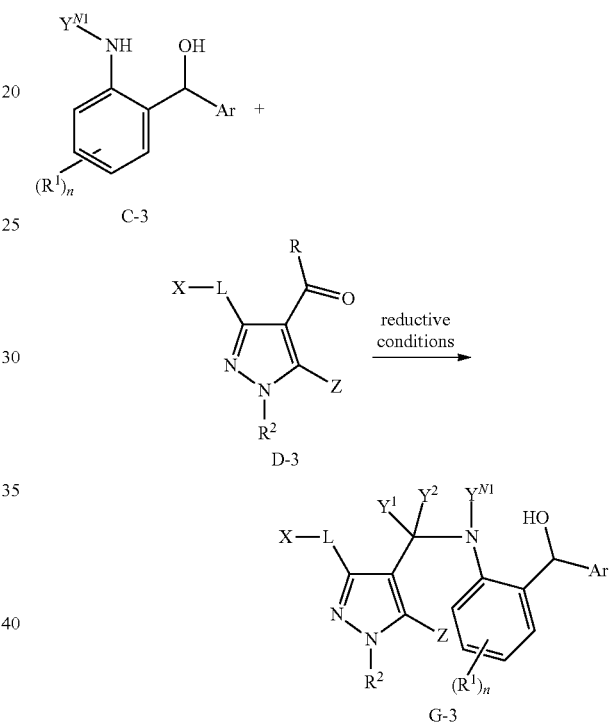

Modifications can also be made to the reaction of Scheme 3. For example, a compound of formula G-4 can be prepared by treating a compound of formula C-4, or a suitable protected derivative thereof (e.g., an acetal derivative), with a compound of formula D-4, or a suitable protected derivative thereof, and "LG" is a leaving group (e.g., any described herein) (see Scheme 4).

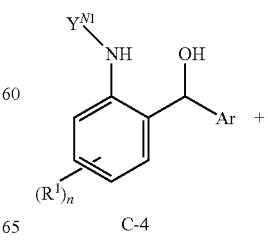

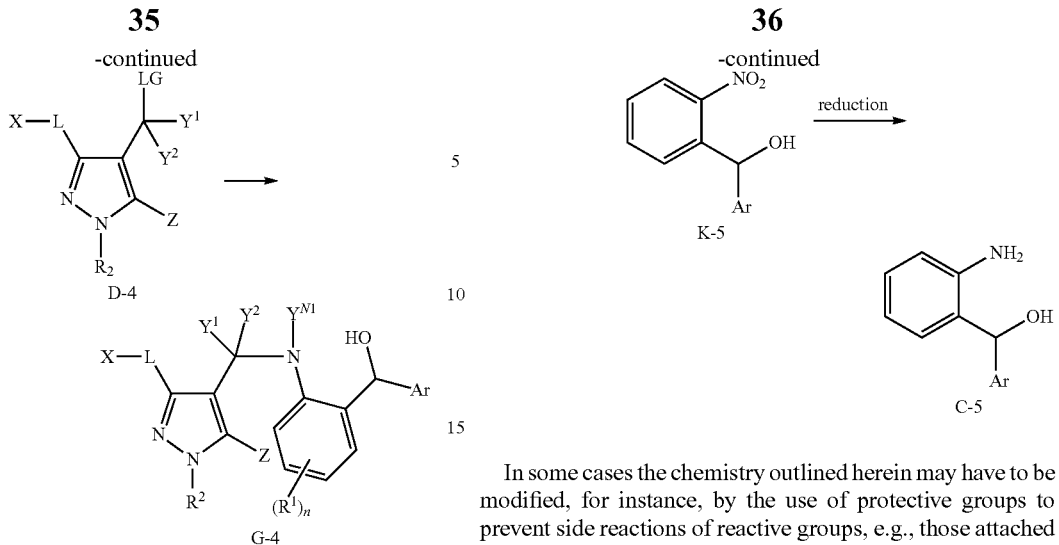

For the reactions in Schemes 1-4, any useful coupling or acylation conditions can be used, such as those used for NH—C(O) coupling in peptide synthesis. Exemplary coupling reagents include one or more of the following reagents: dicyclohexylcarbodiimide (DCC), diisopropylcarbodiimide (DIC), 1-hydroxy-benzotriazole (HOBt), 1-hydroxy-7-azabenzotriazole (HOAt), dimethoxy-1,3,5-triazin-2-yl)-4-methylmorpholin-4-ium chloride (DMTMMCl) either with or without 4-methylmorpholine (NMM), 2-chloro-4,6-dimethoxy-1,3,5-triazine (CDMT) either with or without NMM, O-benzotriazole-N,N,N',N'-tetramethyl-uronium-hexafluoro-phosphate (HBTU), 2-(7-aza-1H-benzotriazole-1-yl)-1,1,3,3-tetramethyluronium hexafluorophosphate (HATU), [(6-chlorobenzotriazol-1-yl)oxy-(dimethylamino)methylidene]-dimethylazanium hexafluorophosphate (HCTU), [benzotriazol-1-yloxy(dimethylamino)methylidene]-dimethylazanium tetrafluoroborate (TBTU), benzotriazol-1-yloxy(tripyrrolidin-1-yl)phosphanium hexafluorophosphate (PyBOP), chloro(tripyrrolidin-1-yl)phosphanium hexafluorophosphate (PyClop), propylphosphonic anhydride (T3P®), (1-cyano-2-ethoxy-2-oxoethylidenaminooxy)dimethylamino-morpholino-carbenium hexafluorophosphate (COMU), ethyl (hydroxyimino)cyanoacetate (Oxyma), and O-[(ethoxycarbonyl)cyanomethylen amino]-N,N,N',N'-tetramethyluronium hexafluorophosphate (HOTU).

The benzhydrol derivative core can be prepared by any useful process. For example, a compound of formula C-5 can be prepared by reacting a compound of formula H-5 with an appropriate Grignard reagent, e.g., a compound of formula J-5, to form an intermediate of formula K-5. Then, the nitro group can be reduced by any useful reductive conditions (e.g., any described herein, such as Pd/C catalysis) to provide a compound of formula C-5. The amino group of formula C-5 could be further modified (e.g., alkylated) to provide a secondary or tertiary amine.

Scheme 5

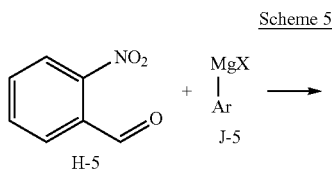

In some cases the chemistry outlined herein may have to be modified, for instance, by the use of protective groups to prevent side reactions of reactive groups, e.g., those attached as substituents. This may be achieved by means of conventional protecting groups as described in *Protective Groups in Organic Chemistry*, McOmie, Ed., Plenum Press, 1973 and in Greene and Wuts, *Protective Groups in Organic Synthesis*, John Wiley & Sons, $3^{rd}$ Edition, 1999.

The compounds of the invention, and intermediates in the preparation of the compounds of the invention, may be isolated from their reaction mixtures and purified (if necessary) using conventional techniques, including extraction, chromatography, distillation, and recrystallization.

The formation of a desired compound salt is achieved using standard techniques. For example, the neutral compound is treated with an acid in a suitable solvent, and the formed salt is isolated by filtration, extraction, crystallization, or any other suitable method.

The formation of solvates of the compounds of the invention will vary depending on the compound and the solvate. In general, solvates are formed by dissolving the compound in the appropriate solvent and isolating the solvate by cooling or adding an antisolvent. The solvate is typically dried or azeotroped under ambient conditions.

Preparation of an optical isomer of a compound of the invention may be performed by reaction of the appropriate optically active starting materials under reaction conditions which will not cause racemization. Alternatively, the individual enantiomers may be isolated by separation of a racemic mixture using standard techniques, such as, for example, fractional crystallization or chiral HPLC.

A radiolabeled compound of the invention may be prepared using standard methods known in the art. For example, tritium may be incorporated into a compound of the invention using standard techniques, such as, for example, by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halogen, suitably iodo, compound using standard palladium-catalyzed stannylation conditions, such as, for example, hexamethylditin in the presence of tetrakis(triphenylphosphine) palladium (0) in an inert solvent, such as dioxane, and at elevated temperatures, preferably 50-100° C.

Pharmaceutical Uses

The present invention features all uses for compounds of the invention, including use in therapeutic methods. The compounds of the invention have useful BTK inhibiting activity, and therefore are useful to treat, prevent, or reduce the risk of, diseases or conditions that are ameliorated by a reduction in BTK activity, such as a B-cell related disorder or a mast cell related disorder (e.g., any disorder described herein).

Cancer

BTK is a key regulator in B-cell development, differentiation, and signaling, as well as in mast cell activation. Accordingly, activation of BTK has been implicated in the pathology of numerous proliferative disorders, including B-cell, mast cell, and other non-B-cell associated cancers.

Exemplary proliferative disorders (e.g., cancers) include leukemia, including acute myeloid leukemia (AML), acute lymphocytic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), and B-cell prolymphocytic leukemia (B-PLL); lymphomas, including Hodgkin and non-Hodgkin lymphoma, such as B-cell lymphomas (e.g., diffuse large B-cell lymphoma (e.g., mediastinal (thymic) large B-cell lymphoma and intravascular large B-cell lymphoma), follicular lymphoma, small lymphocytic lymphoma (SLL), chronic lymphocytic leukemia/small lymphocytic lymphoma (CLL/SLL), mantle cell lymphoma (e.g., relapsed or refractory), marginal zone B-cell lymphomas (e.g., extranodal marginal zone B-cell lymphoma, nodal marginal zone B-cell lymphoma, and splenic marginal zone lymphoma), Burkitt lymphoma, lymphoplasmacytic lymphoma (Waldenstrom macroglobulinemia), hairy cell leukemia, primary central nervous system (CNS) lymphoma, primary effusion lymphoma, and lymphomatoid granulomatosis); myelomas, including multiple myeloma (plasma cell myeloma), plasmacytoma, localized myeloma, and extramedullary myeloma; and other cancers, such as pancreatic neoplasms, including pancreatic exocrine tumors (e.g., ductal adenocarcinoma, signet ring cell carcinomas, hepatoid carcinomas, colloid carcinomas, undifferentiated carcinomas, and undifferentiated carcinomas with osteoclast-like giant cells), pancreatic cystic neoplasms (e.g., mucinous cystadenoma, serous cystadenoma, and mucinous ductal ectasia), pancreatic neuroendocrine tumors (e.g., insulinoma, glucagonoma, gastrinoma (Zollinger-Ellison syndrome), VIPoma, and somatostatinoma), papillary cystic neoplasms of the pancreas, lymphoma of the pancreas, and acinar cell tumors of the pancreas; malignant glioma; and papillary thyroid cancer.

Inflammatory Disorders (Including Autoimmune Disorders)

Inhibition of BTK has been shown to mitigate inflammation and/or suppress the production of inflammatory cytokines. Accordingly, the compounds of the invention can be used to treat or prophylactically treat inflammatory disorders, including autoimmune disorders.

Exemplary inflammatory or autoimmune disorders include rheumatoid arthritis, systemic lupus erythematosus (and associated glomerulonephritis), multiple sclerosis, and asthma. Further exemplary disorders include acute disseminated encephalomyelitis, Addison's disease, allergy, alopecia universalis, Alzheimer's disease, ankylosing spondylitis, antiphospholipid antibody syndrome, aplastic anemia, appendicitis, atherosclerosis, autoimmune arthritis (e.g., rheumatoid arthritis, psoriatic arthritis, ankylosing spondylitis, Still's disease, juvenile arthritis, and mixed and undifferentiated connective tissue diseases), autoimmune hemolytic and thrombocytopenic states (e.g., autoimmune-mediated hemolytic anemia, e.g., warm autoimmune hemolytic anemia, cold autoimmune hemolytic anemia, cold agglutinin disease, and paroxysmal cold hemoglobinuria), autoimmune hepatitis, Behçet's disease, blepharitis, bronchiolitis, bronchitis, bursitis, celiac disease, cervicitis, cholangitis, cholecystitis, chronic fatigue, chronic idiopathic thrombocytopenic purpura (ITP), colitis, conjunctivitis, Crohn's disease, cystitis, dacryoadenitis, dermatitis (including contact dermatitis), dermatomyositis, diabetes, dysautonomia, eczema, encephalitis, endocarditis, endometriosis, endometritis, enteritis, enterocolitis, epicondylitis, epididymitis, fasciitis, fibromyalgia (fibrositis), gastritis, gastroenteritis, gingivitis, glomerulonephritis, Goodpasture's syndrome (and associated glomerulonephritis and pulmonary hemorrhage), Graves' disease, Guillain-Barré syndrome, Hashimoto's thyroiditis, hepatitis, hidradenitis suppurativa, hyperacute rejection of transplanted organs, idiopathic thrombocytopenic purpura (ITP), inflammatory bowel disease (including Crohn's disease and ulcerative colitis), inflammatory pelvic disease, interstitial cystitis, irritable bowel syndrome, juvenile arthritis, juvenile idiopathic arthritis, laryngitis, mastitis, meningitis, multiple vasculitides, myasthenia gravis, myelitis myocarditis, myocarditis, myositis, nephritis, neuromyotonia, oophoritis, opsoclonus-myoclonus syndrome, optic neuritis, orchitis, Ord's thyroiditis, osteitis, osteoarthritis, osteomyelitis, otitis, pancreatitis, Parkinson's disease, parotitis, pericarditis, peritonitis, pharyngitis, phlebitis, pleuritis, pneumonia, pneumonitis, primary biliary cirrhosis, proctitis, prostatitis, psoriasis (including psoriatic lesions in the skin), psoriatic arthritis, pyelonephritis, Reiter's syndrome, rheumatoid arthritis, rhinitis (including allergic rhinitis), rosacea, salpingitis, scleroderma, septic shock, sinusitis, Sjögren's syndrome, skin sunburn, skin sunburn, Still's disease, stomatitis, synovitis, Takayasu's arteritis, temporal arteritis, tendonitis, tissue graft rejection, tonsillitis, urethritis, urticaria, uveitis, uvitis, vaginitis, vasculitis (including antineutrophil cytoplasmic antibodies-associated vasculitis and immune complex mediated vasculitis), vulvitis, vulvodynia, warm autoimmune hemolytic anemia, and Wegener's granulomatosis.

Combination Formulations and Uses Thereof

The compounds of the invention can be combined with one or more therapeutic agents. In particular, the therapeutic agent can be one that treats or prophylactically treats any disorder described herein, such as a B-cell related disorder, cancer, or an inflammatory or autoimmune disorder.

Combination Formulations

In addition to the formulations described herein, one or more compounds of the invention can be used in combination with other therapeutic agents. For example, one or more compounds of the invention can be combined with another therapeutic agent. Exemplary therapeutic agent useful for this purpose include, without limitation, those described in U.S. Pat. Nos. 8,008,309; 7,943,618; 7,884,108; 7,868,018; 7,825,118; 7,642,255; 7,501,410; 7,405,295; 6,753,348; and 6,303,652.

In particular embodiments, the compound of the invention is used in combination with an anti-cancer agent or an anti-inflammatory agent (e.g., a nonsteroidal anti-inflammatory drug, acetaminophen, a gold complex, a corticosteroid, or an immunosuppressant).

Non-limiting, exemplary anti-cancer agents include fludarabine, cyclophosphamide, methotrexate, rituximab, bendamustine, ofatumumab, dasatinib, U0126 ((2Z,3Z)-2,3-bis[amino-(2-aminophenyl)sulfanylmethylidene]butanedinitrile), PD98059 (2-(2-amino-3-methoxyphenyl)chromen-4-one), PD184352 (2-(2-chloro-4-iodoanilino)-N-(cyclopropylmethoxy)-3,4-difluorobenzamide), PD0325901 (N-[(2R)-2,3-dihydroxypropoxy]-3,4-difluoro-2-[(2-fluoro-4-iodophenyl)amino]-benzamide), ARRY-142886 (6-(4- bromo-2-chloroanilino)-7-fluoro-N-(2-hydroxyethoxy)-3-methylbenzimidazole-5-carboxamide), SB 239063 (trans-4-[4-(4-fluorophenyl)-5-(2-methoxy-4-pyrimidinyl)-1H-imidazol-1-yl]cyclohexanol), SP 600125 (anthra[1-9-cd]pyrazol-6(2H)-one), BAY 43-9006 (sorafenib or 4-[4-[[4-chloro-3(trifluoromethyl)phenyl]carbamoylamino]phenoxy]-N-methylpyridine-2-carboxamide), wortmannin, or LY 294002 (2-(4-morpholinyl)-8-phenyl-4H-1-benzopyran-4-one or a hydrochloride salt thereof). Additional non-limiting, exemplary classes of anti-cancer agents include other kinase inhibitors (e.g., a BTK inhibitor, e.g., PCI-32765 (1-[(3R)-3-[4-amino-3-(4-phenoxyphenyl)pyrazolo[3,4-d]pyrimidin-1-yl]piperidin-1-yl]prop-2-en-1-one), LCB 03-0110 ((3-(2-(3-(morpholinomethyl)phenyl)thieno[3,2-b]pyridin-7-ylamino)phenol), (−)-terreic acid ((1R,6S)-3-hydroxy-4-methyl-7-oxabicyclo[4.1.0]hept-3-ene-2,5-dione), LFM-A13 (2-cyano-N-(2,5-dibromophenyl)-3-hydroxy-2-butenamide), staurosporine, and dasatinib), topoisomerase I inhibitors (e.g., camptothecin and topotecan), topoisomerase II inhibitors (e.g., daunomycin and etoposide), alkylating agents (e.g., cyclophosphamide, melphalan, and carmustine (BCNU)), and anti-tubulin agents (e.g., taxol and vinblastine).

Non-limiting, exemplary anti-inflammatory agents include a nonsteroidal anti-inflammatory drug (an NSAID, e.g., non-specific and COX-2 specific cyclooxgenase enzyme inhibitors), acetaminophen, a gold complex, a corticosteroid, and an immunosuppressant. Non-limiting examples of NSAIDs include acemetacin, aspirin, celecoxib, deracoxib, diclofenac, diflunisal, ethenzamide, etodolac, etofenamate, etoricoxib, fenoprofen, flufenamic acid, flurbiprofen, hydroxychloroquine, ibuprofen, indomethacin, isoxicam, kebuzone, ketoprofen, ketorolac, lonazolac, lornoxicam, lumiracoxib, meclofenamic acid, mefenamic acid, meloxicam, metamizol, misoprostol, mofebutazone, naproxen, nabumetone, niflumic acid, piroxicam, oxaprozinpiroxicam, oxyphenbutazone, parecoxib, phenidone, phenylbutazone, piroxicam, propacetamol, propyphenazone, rofecoxib, salicylamide, salsalate, sulfasalazine, sulindac, suprofen, tiaprofenic acid, tenoxicam, tolmetin, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, and 2-(3,5-difluorophenyl)-3-[4-(methylsulfonyl)phenyl]-2-cyclopenten-1-one. Non-limiting examples of gold complexes include aurothioglucose, auranofin disodium aurothiomalate, sodium aurothiomalate, and sodium aurothiosulfate. Non-limiting examples of corticosteroids include cortisone, dexamethasone, methylprednisolone, prednisolone, prednisolone sodium phosphate, and prednisone. Non-limiting examples of immunosuppressants include alkylation agents (e.g., cyclophosphamide), antimetabolites (e.g., azathioprine, methotrexate, leflunomide, and mycophenolate mofetil), antibodies or antibody fragments or derivatives (e.g., an anti-05 monoclonal antibody, such as eculizumab or pexelizumab; and a TNF antagonist, such as entanercept or infliximab, or fragments or derivatives of any of these), and macrolides (e.g., cyclosporine and tacrolimus).

Combination Therapies

A compound of the invention can be used alone or in combination with other agents that have BTK-inhibiting activity, or in combination with other types of treatment (which may or may not inhibit BTK) to treat, prevent, and/or reduce the risk of cancer, an inflammatory disorder, or other disorders that benefit from BTK inhibition. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, $20^{th}$ ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, *acacia*, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

Diagnostic and Screening Assays

In addition to the above-mentioned therapeutic uses, a compound of the invention can also be used in diagnostic assays, screening assays, and as a research tool.

In diagnostic assays, a compound of the invention may be useful in identifying or detecting BTK activity.

In screening assays, a compound of the invention may be used to identify other compounds that inhibit BTK, for example, as first generation drugs. As research tools, the compounds of the invention may be used in enzyme assays and assays to study the extent of BTK activity. Such information may be useful, for example, for diagnosing or monitoring disease states or progression. In such assays, a compound of the invention may also be radiolabeled.

BTK In Vitro Inhibition Assays

The compounds of the present invention have been found to exhibit BTK inhibition. Compounds may be examined for their efficacy in inhibiting kinase activity by a person skilled in the art, for example, by using the methods described in Example 1 and the other examples provided herein or by methods known in the literature (e.g., Mast Cells: Methods and Protocols (eds. G. Krishnaswamy and D.S. Chi), Methods in Molecular Biology, Series 315, Humana Press, pp. 175-192, 2006).

Inhibitory activity can be determined by any useful method. For example, inhibition can be determined by the effect of a test compound on BTK autophosphorylation. Btk and varying concentrations of the test compound can be included in a $[\gamma^{-32}P]$ATP-containing kinase buffer. Autophosphorylation can be analyzed by SDS/PAGE followed by electroblotting and autoradiography, where phosphorylated protein bands can be quantified by densitometry. These assays can be conducted without or with an exogenous substrate (e.g., glutathione S-transferase (GST)-IGα).

In another example, inhibitory activity can be determined by the effect of a test compound on BTK binding. For example, BTK can bind to protein kinase C (PKC) in vivo, where PKC in turn phosphorylates BTK. Accordingly, an exemplary assay to assess BTK-PKC binding includes incubating PKC or cell lysates having PKC (e.g., lysates from human mast cell lines) with glutathione S-transferase (GST)-Btk beads in the absence or presence of the test compound. Then, the extent of Btk-bound PKC can be detected by any useful manner, such as by SDS/PAGE followed by immunoblotting with anti-PKC (MC5) and/or anti-BTK antibodies.

Further examples include use of cellular assays, such as by determining the effect of a test compound on cellular activation. For example, stimulated lymphoid, myeloid, or mast cells (e.g., cells stimulated with a signaling molecule, such as erythropoietin or an antigen, such as IgE) can be incubated with a test compound, and the activation of particular compounds or proteins can be measured. Exemplary compounds and proteins include histamine, leukotriene, cytokines, PKC, Janus tyrosine kinase 2 (Jak2), erythropoietin receptor (EpoR), Stat5, protein kinase B (PKB), and/or mitogen activating protein kinase (Erk1/2). In another example, as activated Btk can be phosphorylated at tyrosine 223 (Y223) and/or tyrosine 551 (Y551), cellular assays can be conducted by staining P-Y223 or P-Y551-positive cells in a population of cells (e.g., by phosphorylation-specific immunochemical staining followed by FACS analysis).

As BTK is a tyrosine kinase, additional useful assays include any tyrosine kinase assay. In particular, commercially available assays include kinase assays that detect formation of ADP, e.g., with luminescent detection, such as in an ADP-Glo™ Kinase Assay (Promega Corp., Madison, Wis.).

Dose response curves can be obtained by incubating BTK with a substrate (e.g., ATP or a binding partner, such as PKC) and increasing (e.g., logarithmically increasing) the concentration of a test compound. In addition, a detectable agent (e.g., a luminescent probe, such as a luciferase/luciferin reaction that measures ATP) can be used to correlate kinase activity (e.g., ATP-to-ADP conversion) with the concentration of the test compound. These data can be used to construct a dose response curve, where $IC_{50}$ is the concentration of the test compound that provides about 50% inhibition.

The following non-limiting examples are illustrative of the present invention.

EXAMPLES

Example 1

BTK Assay

The compounds were assayed for BTK inhibition activity using the Invitrogen™ LanthaScreen® Kinase Binding Assay. In short, the compounds were tested for their ability to displace a tracer (in this case Invitrogen™ Kinase Tracer 236) from the active site of BTK. The BTK protein used in the assay was labeled with europium (Eu), and so displacement was conveniently detected as a loss of Eu-to-tracer FRET (fluorescence resonance energy transfer) signal using a plate reader equipped to measure TR-FRET (time resolved FRET). This displacement assay is commonly used to characterize kinase inhibitors and it is predictive of kinase inhibitory activity.

Several of the compounds were also tested directly for kinase inhibitory activity using the Invitrogen™ Omnia® assay. The Omnia® assay is a real time kinetic assay that uses a phosphate-induced fluorophore to detect transfer of phosphate from ATP to a peptide. Inhibition of kinase activity in this assay reduces the rate of fluorescence increase. Compounds tested in both assays demonstrated similar $IC_{50}$ values. More details and experimental protocols for both assays can be found at invitrogen.com.

Determination of $IC_{50}$ Values

Various compounds of the invention (i.e., compounds of formula (Ia)) were assayed for BTK inhibition activity, as described above, and possessed $IC_{50}$ values less than 1.0 µM. In some embodiments, the compounds possessed $IC_{50}$ values less than 0.9 µM, less than 0.75 µM, less than 0.5 µM, less than 0.3 µM, less than 0.25 µM, less than 0.2 µM, less than 0.15 µM, less than 0.1 µM, less than 0.09 µM, less than 0.08 µM, less than 0.05 µM, less than 0.04 µM, less than 0.03 µM, or less than 0.025 µM. In some embodiments, the compounds possessed $IC_{50}$ values from 0.02 µM to 0.9 µM (e.g., from 0.02 µM to 0.75 µM, from 0.02 µM to 0.5 µM, from 0.02 µM to 0.3 µM, from 0.02 µM to 0.25 µM, from 0.02 µM to 0.2 µM, from 0.02 µM to 0.15 µM, from 0.02 µM to 0.1 µM, from 0.02 µM to 0.09 µM, from 0.02 µM to 0.08 µM, from 0.02 µM to 0.05 µM, from 0.02 µM to 0.04 µM, from 0.02 µM to 0.03 µM, or from 0.02 µM to 0.025 µM).

Example 2

Synthesis of N-(4-(2-amino-2-oxoethyl)phenyl)-4-(((2-(hydroxy(phenyl)methyl)phenyl)amino)methyl)-1H-pyrazole-3-carboxamide (compound 1)

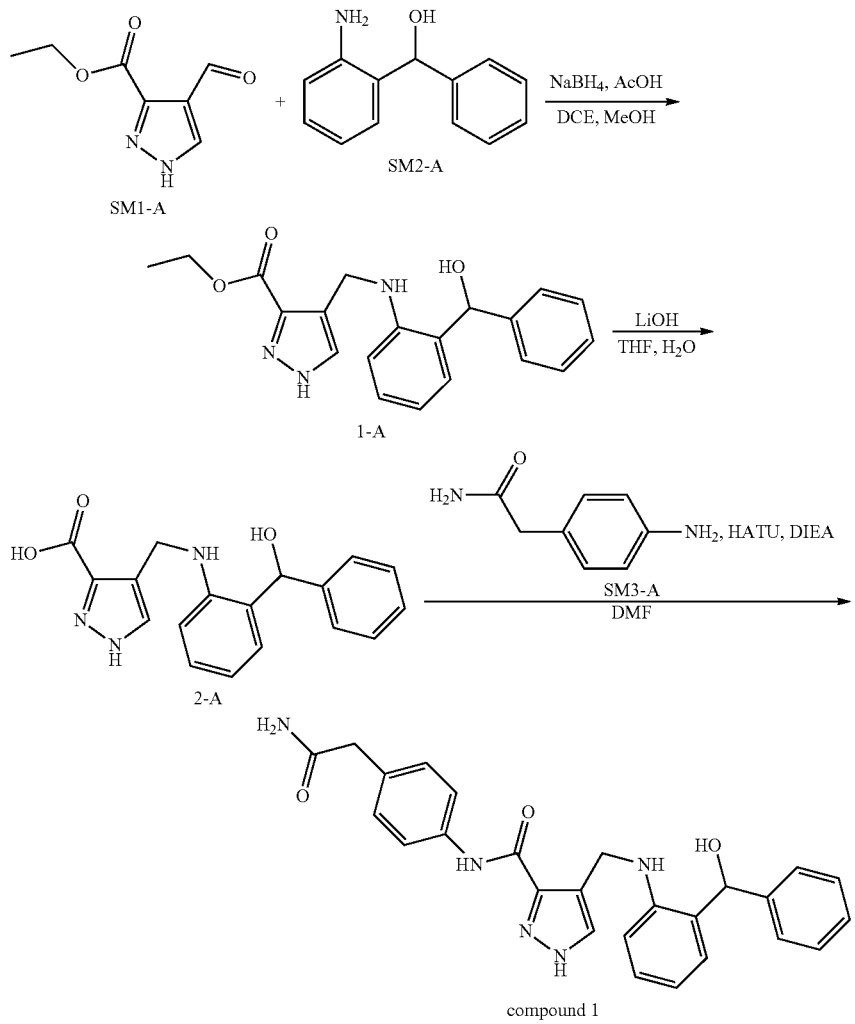

Synthesis of ethyl 4-((2-(hydroxy(phenyl)methyl) phenylamino)methyl)-1H-pyrazole-3-carboxylate (1-A)

To a solution of SM1-A (2 g, 11.9 mmol) and SM2-A (2.37 g, 11.9 mmol) in 1,2-dichloroethane (DCE, 20 mL) was added acetate acid (1 mL) at room temperature (rt). The reaction mixture was stirred at rt for overnight, and then MeOH (10 mL) was added, followed by NaBH$_4$ (1.9 g, 50 mmol). The solution was stirred at rt for another 30 minutes (min); diluted with dichloromethane (DCM, 30 mL); washed with 5% of citric acid (50 mL), NaHCO$_3$ (sat, 50 mL), and brine (50 mL); dried over Na$_2$SO$_4$; and concentrated and purified by column chromatography (petroleum ether:ethyl acetate (PE:EA)=2:1) to give product (1-A) (3.1 g, 74%) as a yellow solid. LC-MS (M+H)$^+$=352.

Synthesis of 4-((2-(hydroxy(phenyl)methyl)phenylamino)methyl)-1H-pyrazole-3-carboxylic acid (2-A)

To a solution of product (1-A) (1.34 g, 3.8 mmol) in THF (30 mL) was added drop-wise a solution of LiOH (0.24 g, 10 mmol) in H$_2$O (30 mL) at 0° C. The reaction mixture was stirred at 50° C. for about 2 h. After cooling, ethyl acetate (20 mL) and H$_2$O (20 mL) were added to the solution. The aqueous layer was separated and acidified with citric acid (to pH=5) and extracted with ethyl acetate (50 mL×3). The combined organic phases were dried over Na$_2$SO$_4$ and concentrated to give crude product (2-A) (1.4 g, 100%) as a light yellow solid. LC-MS (M+H)$^+$=324.

Synthesis of N-(4-(2-amino-2-oxoethyl)phenyl)-4-((2-(hydroxy(phenyl)methyl)phenylamino)methyl)-1H-pyrazole-3-carboxamide (compound 1)

Figure 1B:
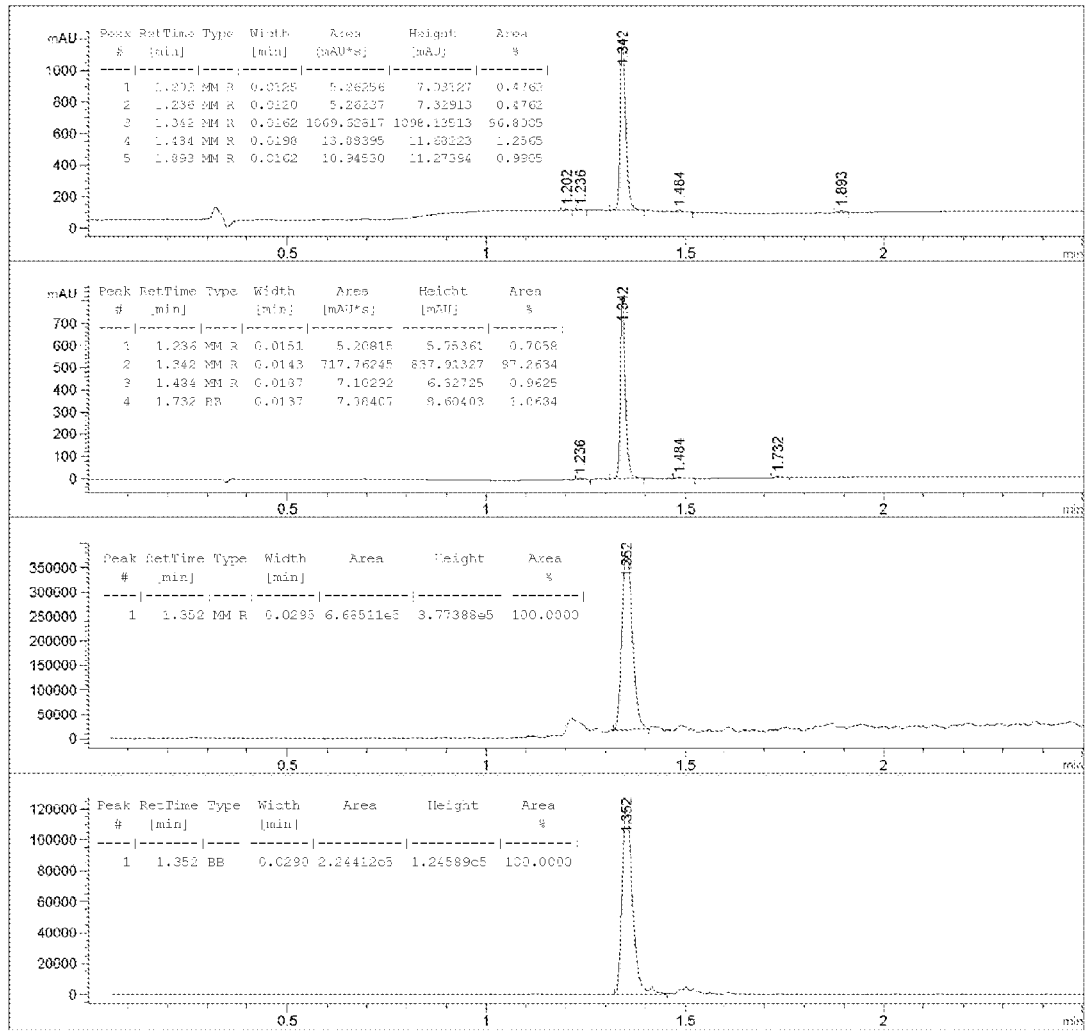
Figure 1C:
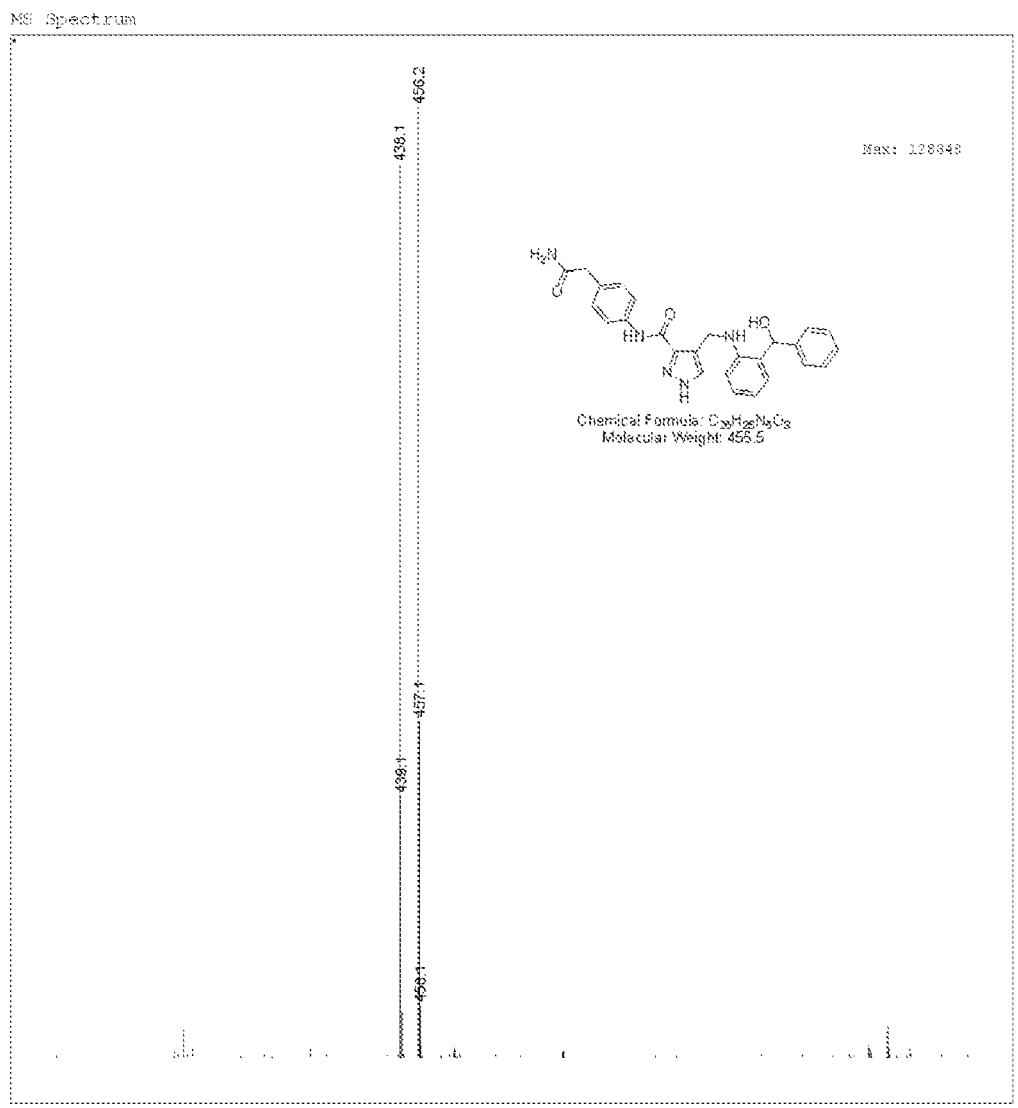
Figure 2A:
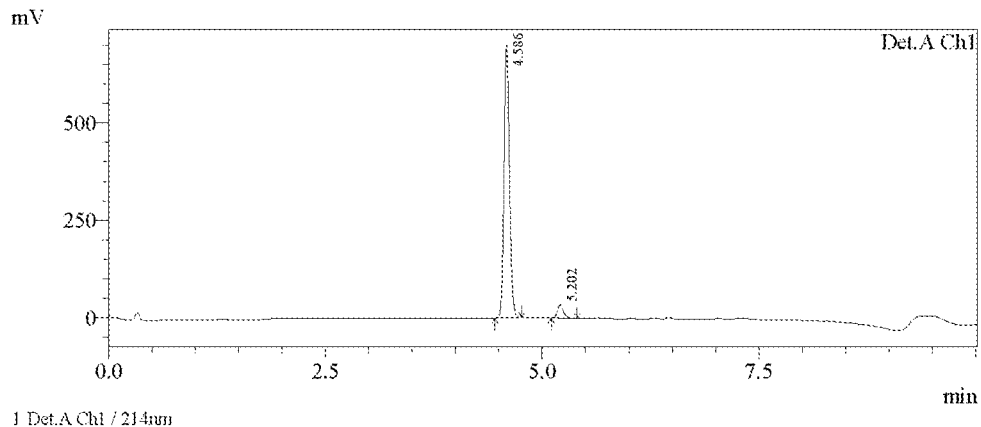
FIGS. 2A-2B are HPLC spectra for compound 1 at 214 nm (FIG. 2A) and at 254 nm (FIG. 2B).
Figure 2B:
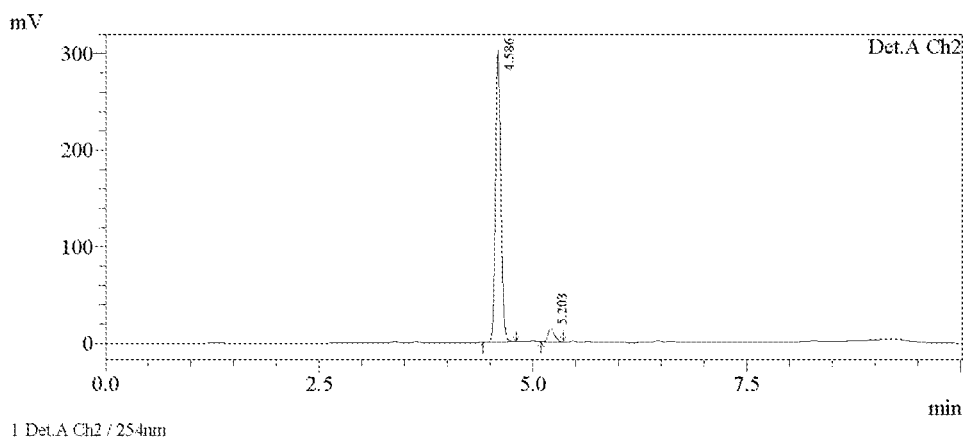

To a solution of product (2-A) (200 mg, 0.62 mol) and SM3-A (111 mg, 0.74 mmol) in DMF (20 mL) was added 2-(7-aza-1H-benzotriazole-1-yl)-1,1,3,3-tetramethyluronium hexafluorophosphate (HATU, 350 mg, 0.93 mmol), followed by diisopropylethylamine (DIPEA, 320 mg, 2.48 mmol) at rt under argon. The reaction mixture was stirred at rt for overnight. The solvent was removed in vacuo and purified by pre-HPLC to give compound 1 (77 mg, 27%) as a white solid. $^1$H NMR (300 MHz, CD$_3$OD): δ 7.56-6.69 (M, 14H), 5.87 (s, 1H), 4.48 (s, 2H), 3.52 (s, 3H). LC-MS (M+H)$^+$=456. $^1$H-NMR (in CD$_3$OD), LC-MS, MS, and HPLC (column: XBridge, 3.5 µm, 2.1×50 mm; mobile phase: H$_2$O (0.05% trifluoroacetic acid, TFA)-acetonitrile (ACN, 0.05% TFA), ACN from 0% to 60% in seven minutes; total flow rate: 0.8 mL/min) spectroscopy experiments were conducted to provide the data in FIGS. 1A-1C and FIGS. 2A-2B for compound 1.

Example 3

Synthesis of 4-(((2-(hydroxy(naphthalen-1-yl)methyl)phenyl)amino)methyl)-N-methyl-1H-pyrazole-3-carboxamide (compound 4)

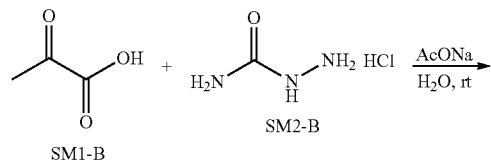

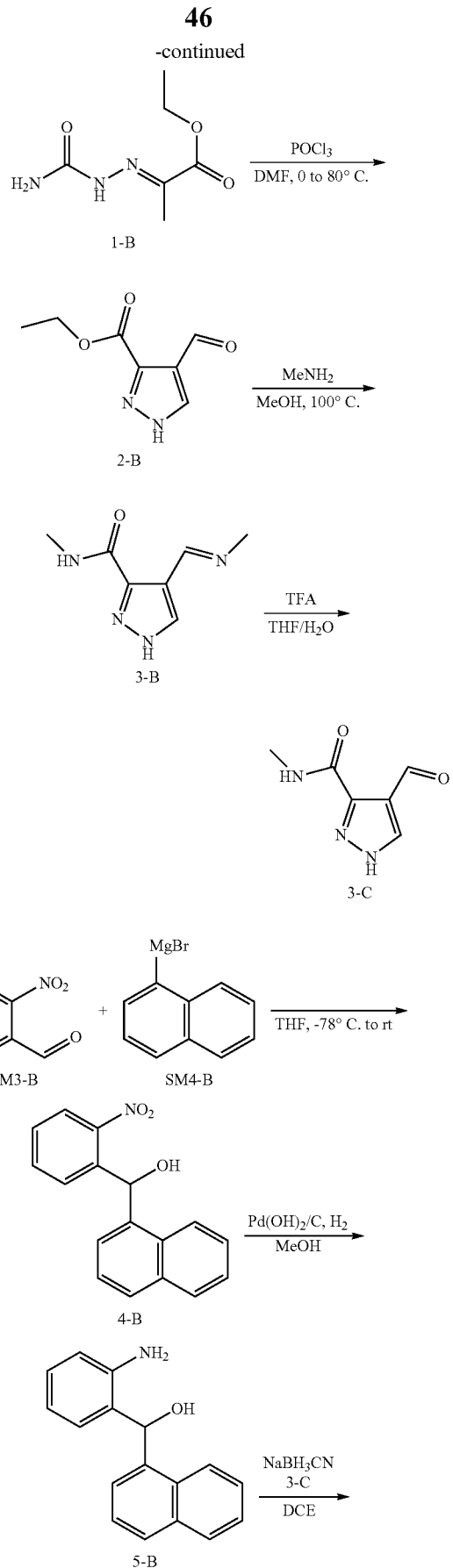

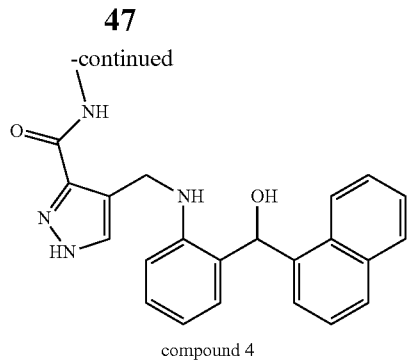

compound 4

Synthesis of ethyl 2-(2-carbamoylhydrazono)propanoate (1-B)

To a solution of SM2-B (100 g, 0.9 mol) and NaOAc (148 g, 1.8 mol) in water (1 L) was added drop-wise SM1-B (105 g, 0.9 mol) at rt over 1 h. A white precipitate was formed while SM1-B was added. The mixture was stirred overnight at rt. The precipitate was filtered, washed with $H_2O$, and dried in air to give crude product (1-B) (200 g, 100%) as a white solid. $^1$H NMR (300 MHz, d-DMSO): δ 9.88 (s, 1H), 6.50 (br, 2H), 4.20 (q, 2H), 2.01 (s, 3H), 1.27 (t, 3H).

Synthesis of ethyl 4-formyl-1H-pyrazole-3-carboxylate (2-B)

$POCl_3$ (532 mL) was added drop-wise to DMF (1 L) at 0° C. over 1 h. The solution was stirred at 0° C. for 1 h, and then product (1-B) (200 g, 0.9 mol) was added in small portions while the reaction temperature was maintained below 5° C. After the addition, the reaction was heated to 80° C. and stirred for another 4 hours. The solution was poured into ice water, and the pH was adjusted to 7 with 2 M NaOH, while maintaining the temperature below 5° C. After standing overnight, the solid was filtered, washed with $H_2O$, and dried in vacuo to give crude product (2-B) (46 g, 30%, for two steps) as a yellow solid. $^1$H NMR (300 MHz, d-DMSO): δ 14.14 (br, 1H), 10.27 (s, 1H), 8.52 (br, 1H), 4.38 (q, 2H), 1.35 (t, 3H). LC-MS $(M+H)^+=169$.

Synthesis of N-methyl-4-((methylimino)methyl)-1H-pyrazole-3-carboxamide (3-B)

The solution of product (2-B) (16.8 g, 0.1 mol) and $MeNH_2$ (0.1 L, 0.2 mol, 2 N in THF) in MeOH (0.2 L) was stirred overnight at 100° C. in a sealed tube. The reaction was monitored by LC-MS until completion. The solvent was removed in vacuo to give crude product (3-B) (17.1 g, 100%) as a brown solid. LC-MS $(M+H)^+=167$.

Synthesis of 4-formyl-N-methyl-1H-pyrazole-3-carboxamide (3-C)

To a solution of product (3-B) (17.1 g, 0.1 mol) in THF (100 mL) was added drop-wise a solution of TFA (57 g, 0.5 mol) in $H_2O$ (100 mL) at rt. The reaction mixture was stirred overnight at rt. The yellow precipitate was filtered, washed with $H_2O$, and dried in air to give crude product (3-C) (12.5 g, 82%, for two steps) as a light yellow solid. $^1$H NMR (300 MHz, d-DMSO): δ 13.93 (br, 1H), 10.33 (br, 1H), 8.52 (br, 1H), 8.44 (s, 1H), 2.79 (d, 3H). LC-MS $(M+H)^+=154$.

Synthesis of naphthalen-1-yl(2-nitrophenyl)methanol (4-B)

The solution of SM3-B (0.9 g, 6 mmol) in THF (20 mL) was cooled to −78° C., and SM4-B (9 mL, 9 mmol, 1 N in THF) was added drop-wise at −78° C. under argon. The cooling bath was removed, and the reaction was warmed to rt and stirred at rt for overnight. The reaction was quenched by saturated $NH_4Cl$ (20 mL) and extracted with ethyl acetate (EA, 20 mL x 2). The combined organic phases were dried over $Na_2SO_4$ and concentrated and purified by column chromatography (CC, PE:EA=30:1 to 5:1) to give product (4-B) (0.5 g, 30%) as a yellow oil. LC-MS $(M-OH)^+=262$.

Synthesis of (2-aminophenyl)(naphthalen-1-yl)methanol (5-B)

To a solution of product (4-B) (0.5 g 1.8 mmol) in MeOH (20 mL) was added $Pd(OH)_2/C$ (0.5 g) at rt. The reaction mixture was stirred at rt under $H_2$ for about 1 h until complete consumption of product (4-B) by LC-MS. The reaction mixture was filtered, and the filtrate was concentrated to give crude product (5-B) (0.4 g, 90%) as a yellow solid. LC-MS $(M-OH)^+=232$.

Synthesis of 4-((2-(hydroxy(naphthalen-1-yl)methyl)phenylamino)methyl)-N-methyl-1H-pyrazole-3-carboxamide (compound 4)

Figure 3A:
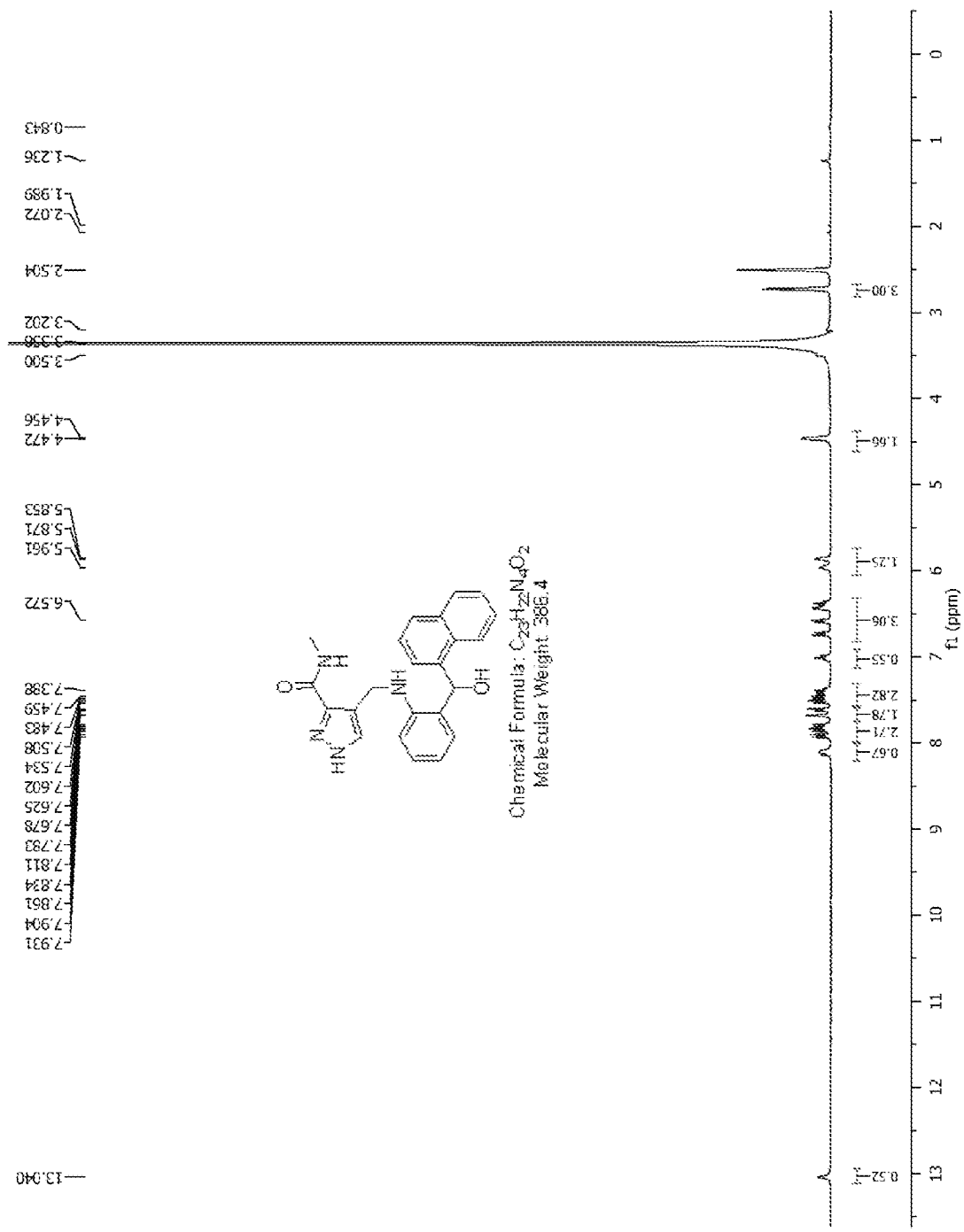
FIGS. 3A-3C are spectra for compound 4, including those for NMR (FIG. 3A), LC-MS (FIG. 3B), and MS (FIG. 3C) spectroscopy.
Figure 3B:
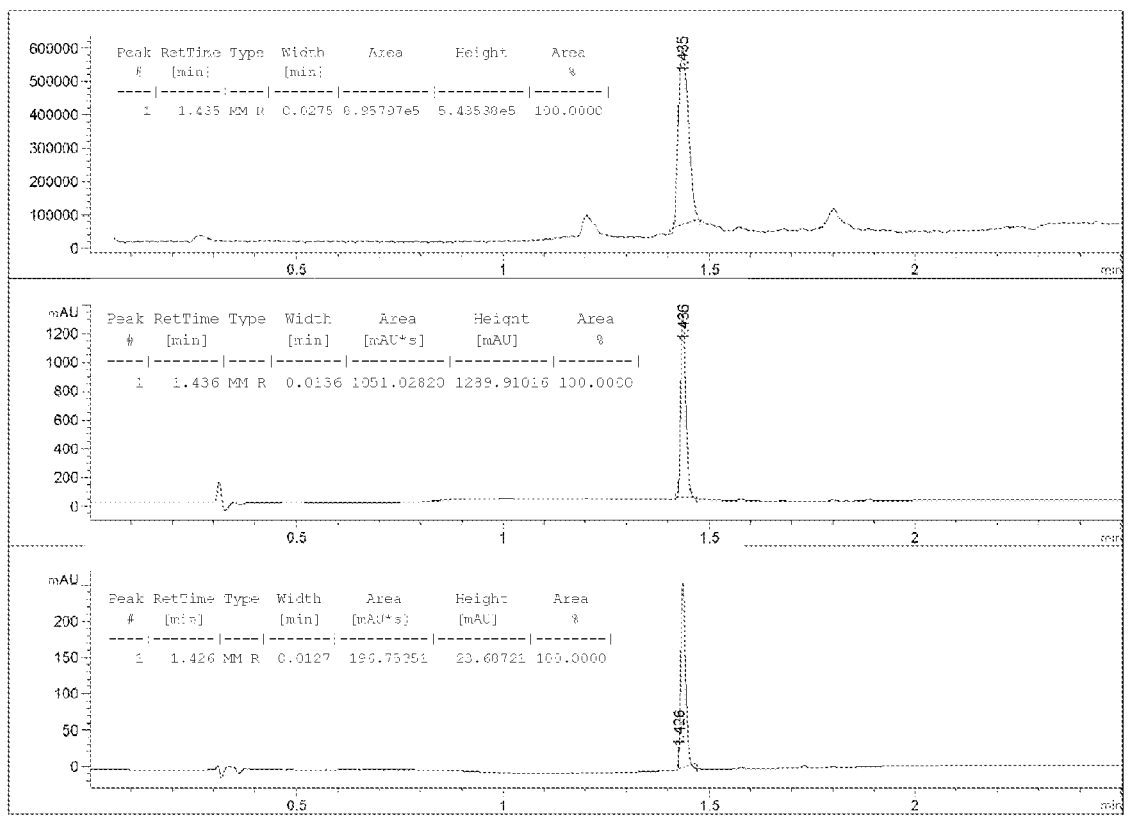
Figure 3C:
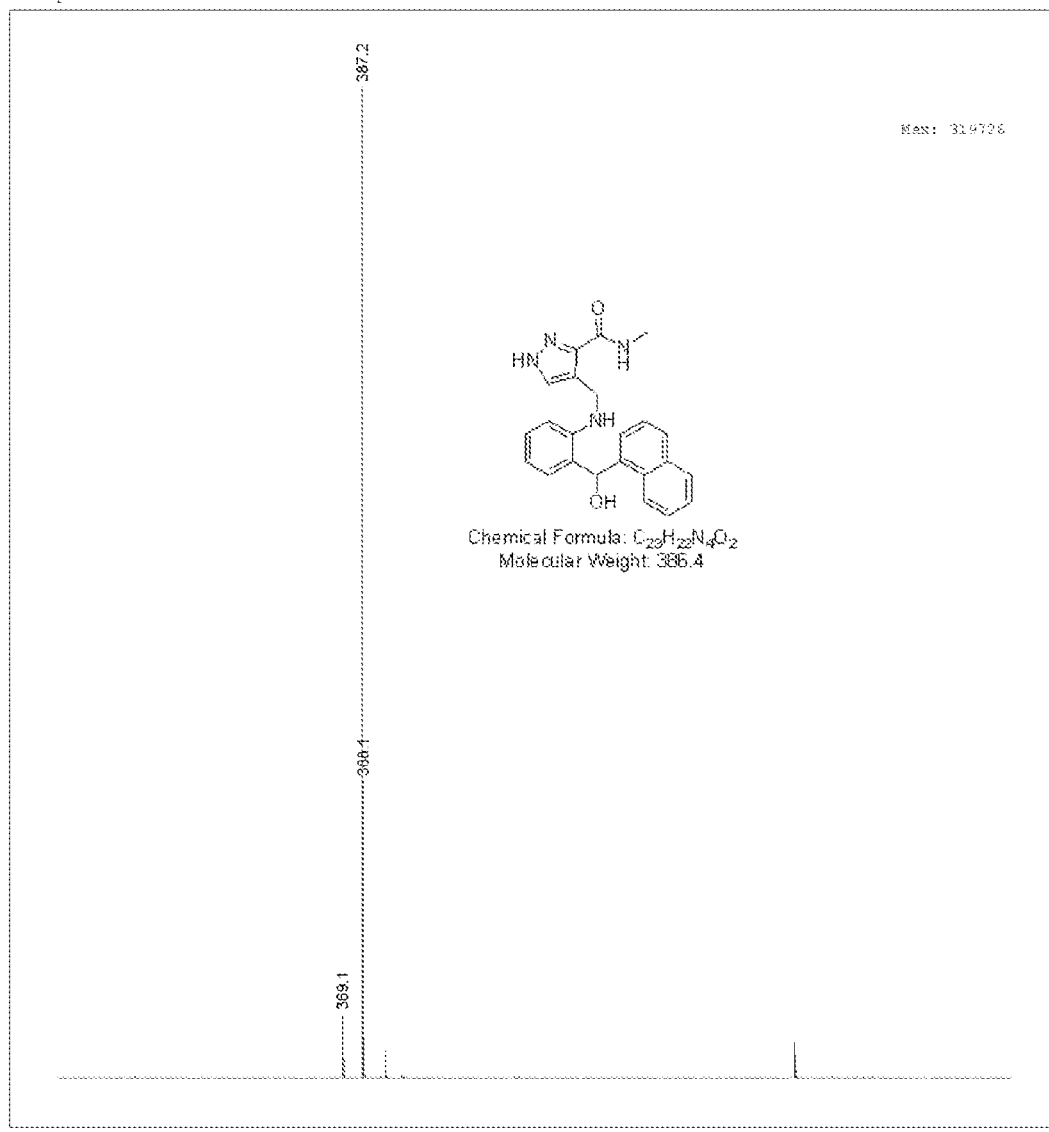
Figure 4A:
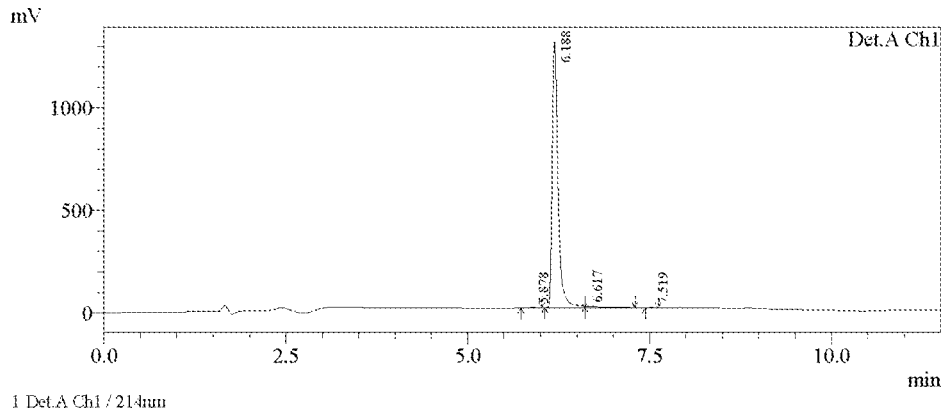
FIGS. 4A-4B are HPLC spectra for compound 4 at 214 nm (FIG. 4A) and at 254 nm (FIG. 4B).
Figure 4B:
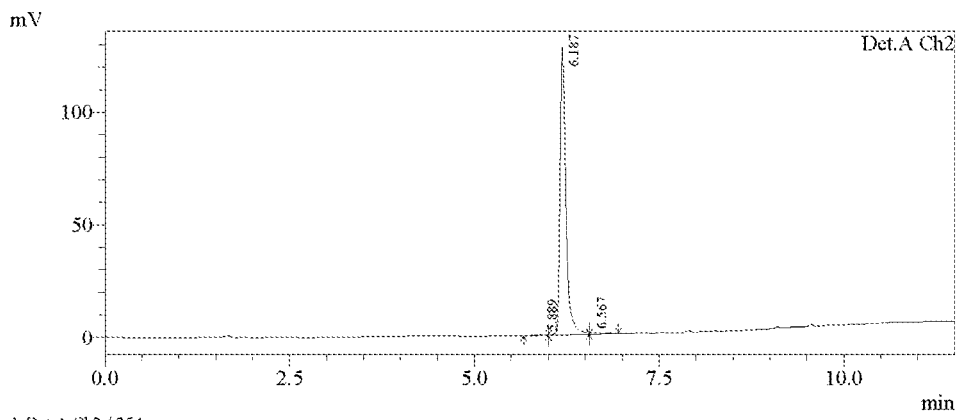

To a solution of product (5-B) (0.4 g 1.6 mmol) in DCE (20 mL) was added product (3-C) (0.25 g, 1.6 mmol) at rt under argon. The reaction was stirred for about 5 h, and then $NaBH_3CN$ (0.5 g, 8 mmol) was added and stirred overnight. The reaction was quenched by saturated $NH_4Cl$ (20 mL) and extracted with DCM/MeOH (20:1 v/v, 20 mL×2). The combined organic phases were dried over $Na_2SO_4$ and concentrated and purified by Prep-HPLC to give compound 4 (22 mg, 5%) as a white solid. $^1$H NMR (300 MHz, d-DMSO): δ 13.04 (br, 1H), 8.14-7.32 (m, 9H), 7.04-6.36 (m, 4H), 5.98-5.85 (m, 2H), 4.47 (d, 2H), 2.72 (d, 3H). LC-MS $(M+H)^+=387$. $^1$H-NMR (in DMSO), LC-MS, MS, and HPLC (column: Thermo, 2.4 μm, 4.6×100 mm; mobile phase: $H_2O$ (0.05% TFA)-ACN (0.05% TFA), ACN from 10% to 100% in eight minutes; total flow rate: 1.0 mL/min) spectroscopy experiments were conducted to provide the data in FIGS. 3A-3C and FIGS. 4A-4B for compound 4.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incor-

What is claimed is:

1. A compound having the formula:

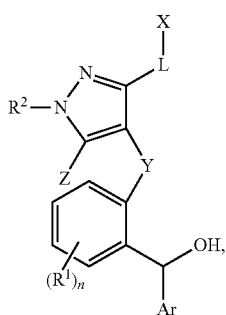

(I)

or a stereoisomer or pharmaceutically acceptable salt thereof, wherein
n is an integer from 0 to 4, and each $R^1$ is, independently, optionally substituted $C_{1-6}$ alkyl, optionally substituted $C_{2-6}$ alkenyl, optionally substituted $C_{2-6}$ alkynyl, optionally substituted halo-$C_{1-6}$ alkyl, optionally substituted $C_{1-6}$ alkoxy, optionally substituted $C_{2-6}$ alkenyloxy, optionally substituted $C_{2-6}$ alkynyloxy, optionally substituted halo-$C_{1-6}$ alkoxy, optionally substituted $C_{1-6}$ alkoxy-$C_{1-6}$ alkyl, optionally substituted $C_{1-7}$ acyl, optionally substituted $C_{1-7}$ acylamino, optionally substituted $C_{1-7}$ acyloxy, optionally substituted $C_{6-10}$ aryl, optionally substituted $C_{1-6}$ alk-$C_{6-10}$ aryl, optionally substituted amino, halo, cyano, nitro, hydroxy, or carboxyl;
Ar is optionally substituted $C_{6-10}$ aryl or optionally substituted $C_{1-12}$ heteroaryl;
$R^2$ is independently, H, optionally substituted $C_{2-6}$ alkenyl, optionally substituted $C_{2-6}$ alkynyl, optionally substituted halo-$C_{1-6}$ alkyl, optionally substituted $C_{1-6}$ alkoxy, optionally substituted $C_{2-6}$ alkenyloxy, optionally substituted $C_{2-6}$ alkynyloxy, optionally substituted halo-$C_{1-6}$ alkoxy, optionally substituted $C_{1-7}$ acyl, optionally substituted amino, halo, cyano, nitro, hydroxy, carboxyl, or an N-protecting group;
Y is —$CY^1Y^2$—$NY^{N1}$-, wherein each $Y^{N1}$ is, independently, H, optionally substituted $C_{1-6}$ alkyl, optionally substituted $C_{2-6}$ alkenyl, optionally substituted $C_{2-6}$ alkynyl, or an N-protecting group; and wherein each $Y^1$ and $Y^2$ is, independently, H, optionally substituted $C_{1-6}$ alkyl, optionally substituted $C_{2-6}$ alkenyl, or optionally substituted $C_{2-6}$ alkynyl; or wherein the combination of $Y^1$ and $Y^2$ can together form oxo or optionally substituted $C_{1-7}$ spirocyclyl;
Z is H, optionally substituted $C_{1-6}$ alkyl, optionally substituted $C_{2-6}$ alkenyl, optionally substituted $C_{2-6}$ alkynyl, optionally substituted halo-$C_{1-6}$ alkyl, optionally substituted $C_{1-6}$ alkoxy, optionally substituted $C_{2-6}$ alkenyloxy, optionally substituted $C_{2-6}$ alkynyloxy, optionally substituted halo-$C_{1-6}$ alkoxy, optionally substituted $C_{1-6}$ alkoxy-$C_{1-6}$ alkyl, optionally substituted $C_{1-7}$ acyl, optionally substituted $C_{1-7}$ acylamino, optionally substituted $C_{1-7}$ acyloxy, optionally substituted $C_{6-10}$ aryl, optionally substituted $C_{1-6}$ alk-$C_{6-10}$ aryl, optionally substituted amino, halo, cyano, nitro, hydroxy, or carboxyl;
L is optionally substituted $C_{1-10}$ alkylene, optionally substituted $C_{1-10}$ heteroalkylene, —$NR^{L3}$—C(O)—, —C(O)—$NR^{L3}$—, —$NR^{L3}$—$CR^{L1}R^{L2}$—, —$CR^{L1}R^{L2}NR^{L3}$—, or a bond, wherein each $R^{L1}$ and $R^{L2}$ is, independently, H, optionally substituted $C_{1-6}$ alkyl, optionally substituted $C_{2-6}$ alkenyl, optionally substituted $C_{2-6}$ alkynyl; or wherein the combination of $R^{L1}$ and $R^{L2}$ can together form oxo or optionally substituted $C_{1-7}$ spirocyclyl; and wherein each $R^{L3}$ is, independently, H, optionally substituted $C_{1-6}$ alkyl, optionally substituted $C_{2-6}$ alkenyl, optionally substituted $C_{2-6}$ alkynyl, or an N-protecting group; and
X is optionally substituted $C_{1-6}$ alkyl, optionally substituted $C_{3-8}$ cycloalkyl, optionally substituted $C_{6-10}$ aryl, or optionally substituted $C_{1-12}$ heterocyclyl.

2. The compound of claim 1, wherein
n is an integer from 0 to 2;
Ar is optionally substituted $C_{6-10}$ aryl or optionally substituted $C_{1-12}$ heteroaryl;
each $Y^1$ and $Y^2$ is, independently, H or optionally substituted $C_{1-6}$ alkyl;
Z is H, optionally substituted $C_{1-6}$ alkyl, optionally substituted halo-$C_{1-6}$ alkyl, or halo;
L is —NH—C(O)—, —C(O)—NH—, —NH—$CR^{L1}R^{L2}$—, —$CR^{L1}R^{L2}$—NH—, or a bond, wherein each $R^{L1}$ and $R^{L2}$ is, independently, H or optionally substituted $C_{1-6}$ alkyl; and
X is optionally substituted $C_{1-6}$ alkyl, optionally substituted $C_{6-10}$ aryl, or optionally substituted $C_{1-12}$ heterocyclyl.

3. The compound of claim 1, wherein said compound has the formula:

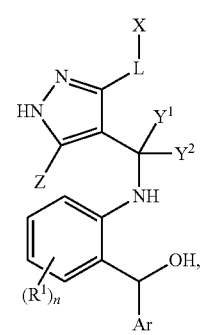

(Ia)

or a pharmaceutically acceptable salt thereof.

4. The compound of claim 1, wherein said compound has the formula:

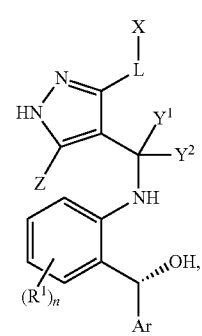

(Ib)

or a pharmaceutically acceptable salt thereof.

5. The compound of claim 1, wherein said compound has the formula:

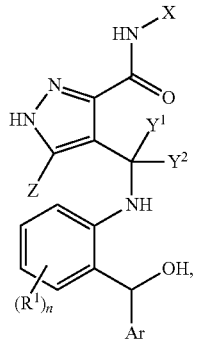

(IIa)

or a stereoisomer or pharmaceutically acceptable salt thereof.

6. The compound of claim 1, wherein said compound has the formula:

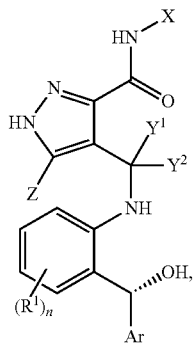

(IIb)

or a pharmaceutically acceptable salt thereof.

7. The compound of claim 1, wherein n is 0.

8. The compound of claim 1, wherein Ar has the formula:

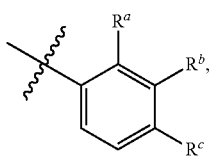

(III)

and
wherein the combination of $R^a$ and $R^b$ or the combination of $R^b$ and $R^c$ can together form optionally substituted $C_{6-10}$ aryl or optionally substituted $C_{1-12}$ heterocyclyl.

9. The compound of claim 1, wherein Ar is optionally substituted $C_{1-12}$ heteroaryl.

10. The compound of claim 1, wherein Ar is selected from the group consisting of optionally substituted phenyl, optionally substituted pyridyl, optionally substituted pyrimidinyl, optionally substituted pyrazinyl, optionally substituted pyridazinyl, optionally substituted naphthyl, optionally substituted indenyl, optionally substituted anthryl, optionally substituted phenanthryl, optionally substituted quinolyl, optionally substituted isoquinolyl, optionally substituted quinoxalinyl, optionally substituted quinazolinyl, optionally substituted cinnolinyl, optionally substituted phthalazinyl, and optionally substituted quinolizinyl.

11. The compound of claim 10, wherein Ar is optionally substituted phenyl, optionally substituted naphthyl, optionally substituted quinolyl, or optionally substituted isoquinolyl.

12. The compound of claim 11, wherein Ar is substituted with $C_{1-6}$ alkyl, halo-$C_{1-6}$ alkyl, $C_{1-6}$ alkoxy, halo-$C_{1-6}$ alkoxy, or halo.

13. The compound of claim 1, wherein each of $Y^1$, $Y^2$, and Z, if present, is, independently, H or optionally substituted $C_{1-6}$ alkyl, or wherein the combination of $Y^1$ and $Y^2$ can together form oxo or spirocyclopropyl.

14. The compound of claim 1, wherein X is optionally substituted $C_{6-10}$ aryl or optionally substituted $C_{1-12}$ heteroaryl.

15. The compound of claim 14, wherein X is optionally substituted phenyl.

16. The compound of claim 15, wherein X is unsubstituted phenyl or phenyl substituted with a substituent selected from the group consisting of $C_{1-6}$ alkyl, halo-$C_{1-6}$ alkyl, $C_{1-6}$ alkoxy, halo-$C_{1-6}$ alkoxy, halo, $C_{1-12}$ heterocyclyl, —$(CH_2)_m$—$CO_2R^{X1}$, —$(CH_2)_m$—$C(O)$—$NR^{X1}R^{X2}$, and —$(CH_2)_m$—$NR^{X1}$—$C(O)$—$R^{X2}$, wherein m is an integer from 0 to 4 and each $R^{X1}$ and $R^{X2}$ is, independently, H or optionally substituted $C_{1-6}$ alkyl.

17. The compound of claim 14, wherein X is selected from the group consisting of optionally substituted quinoxalinyl, optionally substituted quinazolinyl, optionally substituted cinnolinyl, optionally substituted phthalazinyl, optionally substituted quinolyl, optionally substituted isoquinolyl, optionally substituted benzoxazolyl, optionally substituted benzimidazolyl, optionally substituted benzothiazolyl, optionally substituted benzothiadiazolyl, optionally substituted indolyl, optionally substituted indazolyl, optionally substituted benzofuranyl, optionally substituted isobenzofuranyl, and optionally substituted benzothienyl.

18. A compound having the formula:

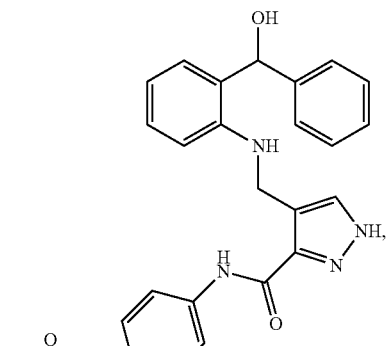

1

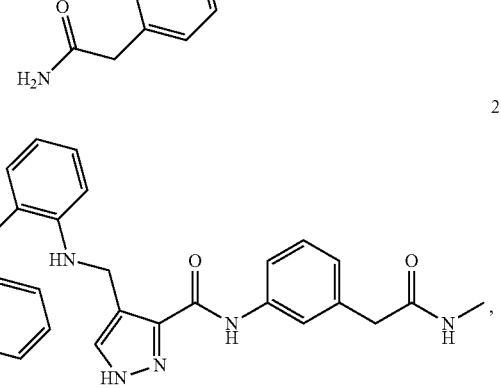

2

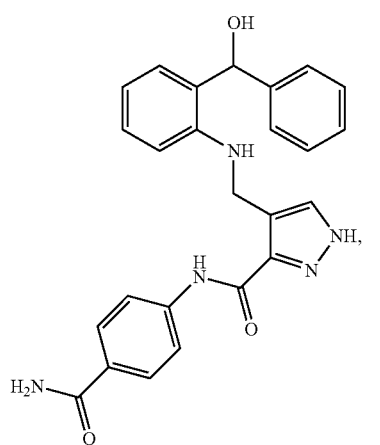
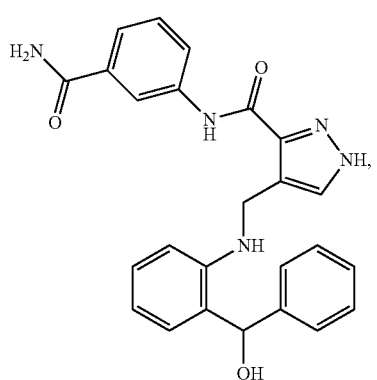
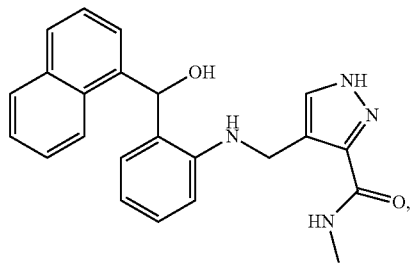
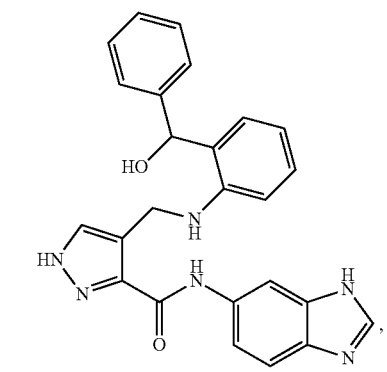
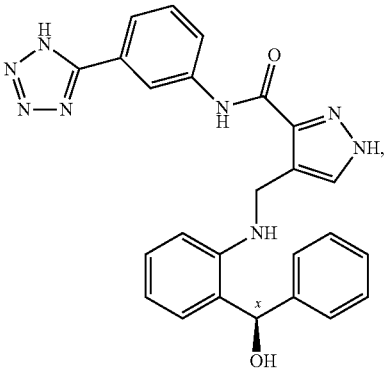
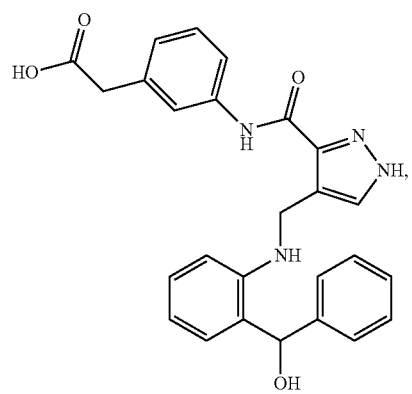
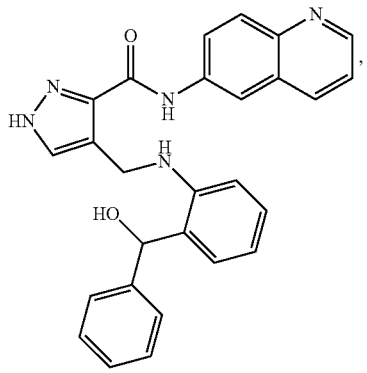

-continued
11
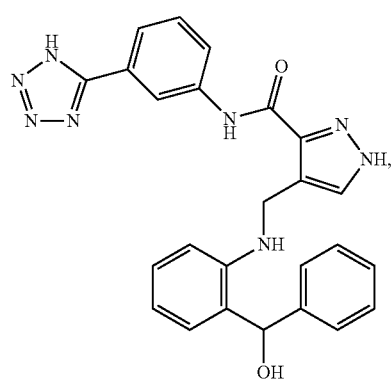
12
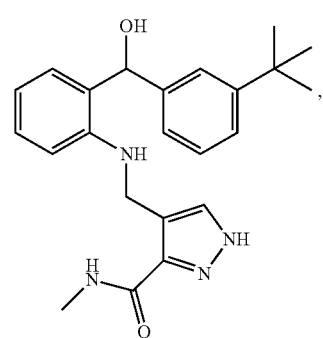
13
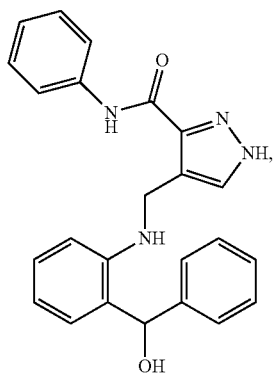
14
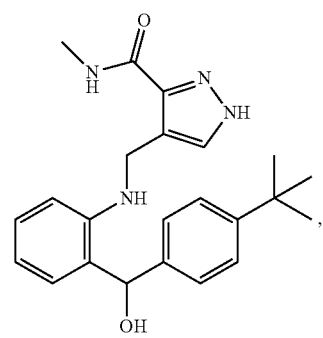
-continued
15
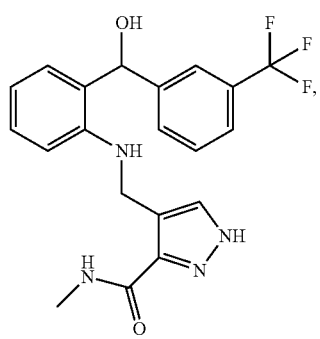
16
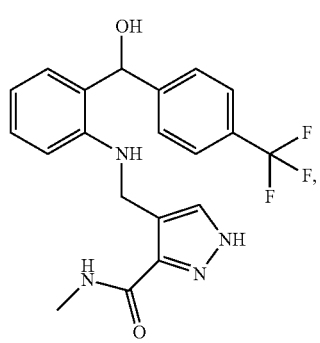
17
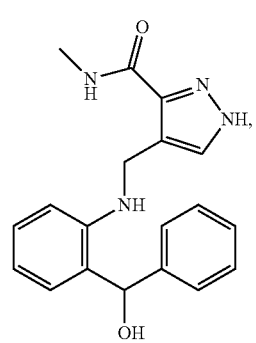
18
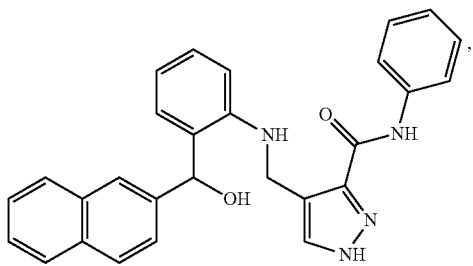

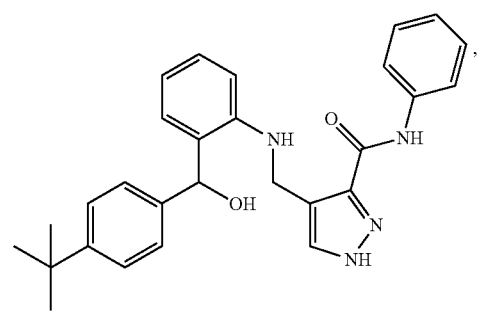

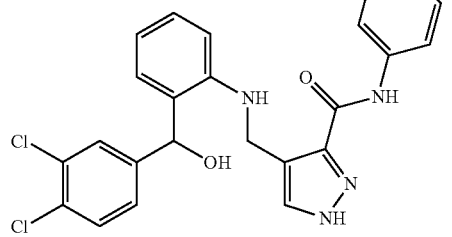

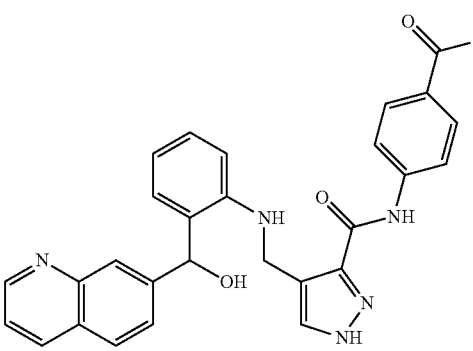

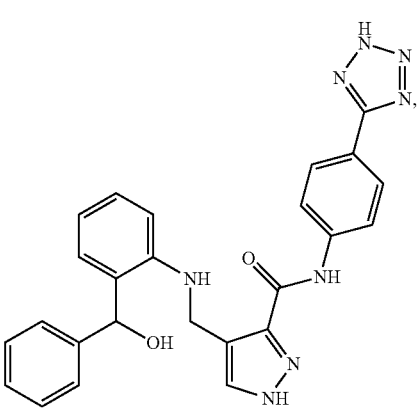

or a stereoisomer or pharmaceutically acceptable salt thereof.

19. A pharmaceutical composition comprising the compound of claim 1, or a stereoisomer, pharmaceutically acceptable salt thereof, and a pharmaceutically acceptable excipient.

20. A method of inhibiting Bruton's tyrosine kinase (BTK) in a subject in need thereof, wherein said method comprises administering an effective amount of the compound of claim 1, or a stereoisomer, pharmaceutically acceptable salt, or pharmaceutical composition thereof to said subject.

21. A method of treating lymphoma in a subject in need thereof by inhibiting Bruton's tyrosine kinase (BTK), said method comprising administering an effective amount of a compound of claim 1, or a stereoisomer, pharmaceutically acceptable salt, or pharmaceutical composition thereof, to said subject.

22. The method of claim 21, wherein said lymphoma is non-Hodgkin lymphoma, B-cell lymphoma, or small lymphocytic lymphoma.

* * * * *